(12) United States Patent
Hu et al.

(10) Patent No.: US 12,391,661 B2
(45) Date of Patent: *Aug. 19, 2025

(54) CYSTINE DIAMIDE ANALOGS FOR THE PREVENTION OF CYSTINE STONE FORMATION IN CYSTINURIA

(71) Applicant: Rutgers, The State University of New Jersey, New Brunswick, NJ (US)

(72) Inventors: Longqin Hu, Belle Mead, NJ (US); Amrik Sahota, Hillsborough, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,376

(22) Filed: Aug. 22, 2022

(65) Prior Publication Data

US 2023/0002337 A1 Jan. 5, 2023

Related U.S. Application Data

(60) Continuation of application No. 17/068,354, filed on Oct. 12, 2020, now Pat. No. 11,420,949, which is a division of application No. 15/248,912, filed on Aug. 26, 2016, now Pat. No. 10,836,737, which is a division of application No. 14/146,103, filed on Jan. 2, 2014, now Pat. No. 9,428,453.

(60) Provisional application No. 61/748,323, filed on Jan. 2, 2013.

(51) Int. Cl.
 C07D 295/185 (2006.01)
 C07C 323/60 (2006.01)
 C07D 211/16 (2006.01)

(52) U.S. Cl.
 CPC ........ *C07D 295/185* (2013.01); *C07C 323/60* (2013.01); *C07D 211/16* (2013.01); C07C 2601/02 (2017.05)

(58) Field of Classification Search
 CPC .. C07D 295/185; C07D 211/16; C07C 323/60
 See application file for complete search history.

(56) References Cited

U.S. PATENT DOCUMENTS

| 5,661,129 | A | 8/1997 | Feelisch et al. |
| 5,801,175 | A | 9/1998 | Afonso et al. |
| 6,034,135 | A | 3/2000 | Schwartz et al. |
| 6,214,827 | B1 | 4/2001 | Afonso et al. |
| 9,428,453 | B2 * | 8/2016 | Hu .................. C07C 323/60 |
| 10,836,737 | B2 | 11/2020 | Hu et al. |
| 2009/0124667 | A1 | 5/2009 | Ansorge et al. |
| 2014/0187546 | A1 | 7/2014 | Hu et al. |

FOREIGN PATENT DOCUMENTS

| JP | 2005-529959 A | 10/2005 |
| WO | 2021119475 A1 | 6/2021 |

OTHER PUBLICATIONS

Registry No. 7729-20-6, File Registry on STN, entered STN Nov. 16, 1984.*
Registry No. 53267-39-3, File Registry on STN, entered STN Nov. 16, 1984.*
Bhuyan et al., Org. Biomol. Chem., Oct. 2012, 2237-2247.
Burth, et al: "New Tripodal N3S Ligands and Some Zinc Complexes Thereof", Eur. J. Inorg. Chem., 1998, pp. 1759-1764.
Menger et al., J. Am. Chem. Soc. 2000, 122, 11679-11691.
Pubchem, SID 32606358, Available Date: Dec. 5, 2007 [retrieved on Jan. 11, 2021]. Retrieved from the Internet: <URL: https://pubchem.ncbi.nlm.nih.gov/substance/32606358>.
Ranganathan, et al.: "Norbornene-Constrained Cyclic Peptides with Hairpin Architecture: Design, Synthesis, Conformation, and Membrane Ion Transport", J. Org. Chem., 2000, vol. 65, pp. 365-374.
Yang, et al: "Design, synthesis, and evaluation of L-cystine diamides as L-cystine crystallization inhibitors for cystinuria", Bioorganic & Medicinal Chemistry Letters 28 (2018) pp. 1303-1308, https://doi.org/10.1016/j.bmcl.2018.03.024.
Allen et al: "A semisynthetic epitope for kinase substrates", Nature Methods, (Jun. 2007), 4(6), pp. 511-516.
Hu et al: L-Cystine Diamides as L-Cystine Crystallization Inhibitors for Cystinuria, Journal of Medicinal Chemistry, (2016), 59(15), pp. 7293-7298.

(Continued)

*Primary Examiner* — Rebecca L Anderson
(74) *Attorney, Agent, or Firm* — FOX ROTHSCHILD LLP

(57) ABSTRACT

Cystine analogs that improve the solubility of L-cystine in urine for treatment of cystinuria and which have the structure:

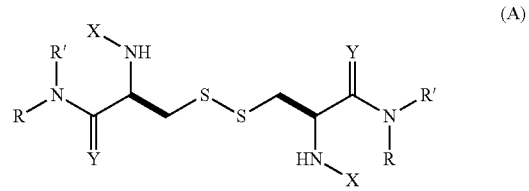

(A)

and pharmaceutically acceptable salts, solvates and prodrugs thereof, wherein
 each R and R' pair are independently selected from (i) or (ii);
 (i) R and R' are independently selected from hydrogen, substituted or unsubstituted alkyl, substituted or unsubstituted alkenyl, substituted or unsubstituted alcohol, substituted or unsubstituted aryl, substituted or unsubstituted cycloalkyl, substituted or unsubstituted heterocyclic, and substituted or unsubstituted heteroaryl, or
 (ii) R and R' together form a substituted or unsubstituted heterocyclic ring structure, or a substituted or unsubstituted heteroaryl ring structure;
 X is hydrogen, or an alkyl; and Y is O or S.

8 Claims, 11 Drawing Sheets

(56) References Cited

OTHER PUBLICATIONS

Lioe et al: "A Novel Salt Bridge Mechanism Highlights the Need for Nonmobile Proton Conditions to Promote Disulfide Bond Cleavage in Protonated Peptides Under Low-Energy Collisional Activation", Journal of the American Society for Mass Spectrometry, (2007), 18(6), pp. 1109-1123.
Poloni et al: "Role of Molecular Recognition in L-Cystine Crystal Growth Inhibition", Crystal Growth & Design, (2017), 17(5), 2767-2781.
Sharma et al: "Synthesis and Anticancer Activity of Some L-Cystine Derivatives", Indian Journal of Pharmaceutical Sciences, (May-Jun. 2002), 64(3), 200-204.
Takagi et al: "Circular dichroism of a model compound of L-cystine residue. N, N'-diacetyl-L-cystine bismethylamide", Biochimica et Biophysica Acta, Protein Structure, (1973), 310(1), pp. 11-19.
File Registry on STN: "Registry No. 639066-12-9", Entered STN: Jan. 19, 2004.

\* cited by examiner

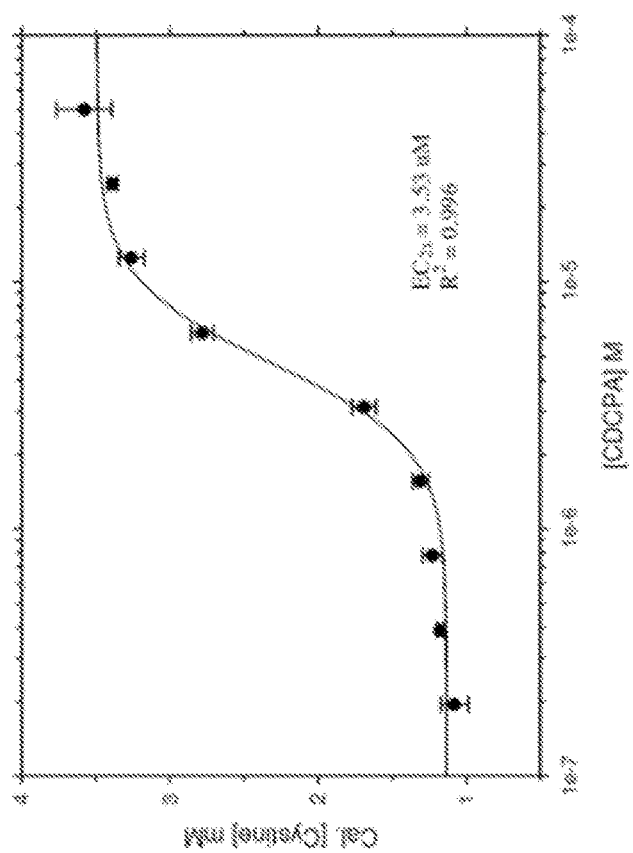
Fig. 2(b)
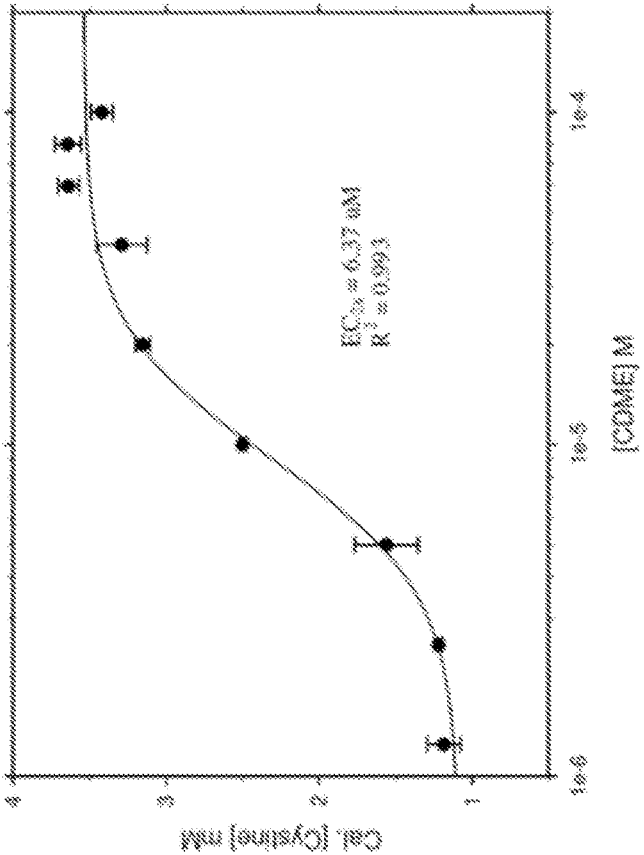
Fig. 2(a)

| LH# | Name | Structure | $EC_{2x}$ (μM)[a] | Ratio[b] |
|---|---|---|---|---|
| Control | CDME | 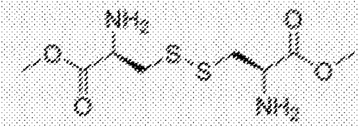 | 6.37 | 1.00 |
| LH704 | CDCPA | 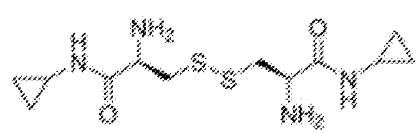 | 3.53 | 1.80 |
| LH706 | CDPIP | 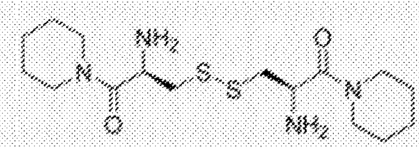 | 1.59 | 4.01 |
| LH707 | CDMOR | 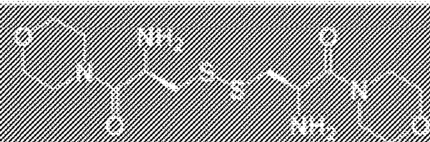 | 0.856 | 7.44 |
| LH708 | CDNME | 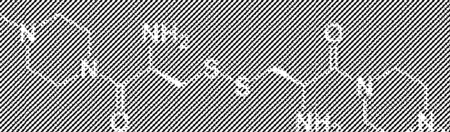 | 0.261 | 24.4 |
| LH709 | CDEOA | 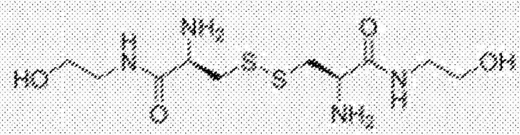 | 2.02 | 3.15 |

[a] $EC_{2x}$ refers to the concentration required to double the aqueous solubility of cystine.
[b] Ratio refers to the improvement in potency over the control CDME.

Fig. 4

LH708 10/23-10/29/13 urine

A-before B-after
Approximate Volume

| Mouse # | Gender | | Before (A) | After (B) | uL of A pooled as control |
|---|---|---|---|---|---|
| 6254 M | SLC(+/+) | 6/28/2013 | 800 | 1000 | 200 |
| 6255 M | SLC(+/+) | 6/28/2013 | 500 | 600 | |
| 6256 M | SLC(+/+) | 6/28/2013 | 900 | 500 | 300 |
| 6260 M | SLC(+/+) | 7/5/2013 | 600 | 700 | 100 |
| 6261 M | SLC(+/+) | 7/5/2013 | 500 | 1100 | |
| 6205 M | SLC(-/-) | 7/5/2013 | 600 | 600 | 200 |
| 6207 M | SLC(-/-) | 7/5/2013 | 250 | 800 | |
| 6210 M | SLC(-/-) | 7/11/2013 | 150 | 200 | 100 |
| 6211 M | SLC(-/-) | 7/11/2013 | 400 | 500 | |
| 6213 M | SLC(-/-) | 7/11/2013 | 200 | 400 | |
| | | Total urine vol | 4900 | 6400 | 900 |

LH707 11/15-11/21/13 urine

| Mouse # | Gender | | Before (A) | After (B) | uL of A pooled as control |
|---|---|---|---|---|---|
| 6274 M | SLC(+/+) | 8/3/2013 | 350 | 150 | 200 |
| 6275 M | SLC(+/+) | 8/3/2013 | 700 | 700 | |
| 6276 M | SLC(+/+) | 8/3/2013 | 800 | 600 | 200 |
| 6277 M | SLC(+/+) | 8/3/2013 | 400 | 500 | |
| 6281 M | SLC(-/-) | 8/3/2013 | 800 | 450 | 300 |
| 6282 M | SLC(-/-) | 8/3/2013 | 500 | 550 | |
| 6284 M | SLC(-/-) | 8/3/2013 | 700 | 400 | 200 |
| 6285 M | SLC(-/-) | 8/3/2013 | 350 | 200 | |
| | | Total urine vol | 4600 | 3550 | 900 |

Fig. 8

| Amino Acids | | Mean | SEM | N | P |
|---|---|---|---|---|---|
| Cystine | Before | 4045 | 1410 | 6 | |
| | After | 7135 | 980 | 6 | *0.0328 |
| Ornithine | Before | 5316 | 443 | 6 | |
| | After | 5720 | 430 | 6 | 0.3045 |
| Lysine | Before | 24904 | 6373 | 6 | |
| | After | 22596 | 2076 | 6 | 0.6942 |
| Arginine | Before | 50484 | 32180 | 6 | |
| | After | 20446 | 1572 | 6 | 0.4112 |
| Proline | Before | 88 | 18 | 6 | |
| | After | 121 | 30 | 6 | 0.2968 |
| Valine | Before | 127 | 31 | 6 | |
| | After | 193 | 41 | 6 | 0.3327 |
| Leucine | Before | 245 | 33 | 6 | |
| | After | 296 | 39 | 6 | 0.4668 |
| Phenylalanine | Before | 44 | 8 | 6 | |
| | After | 103 | 32 | 6 | 0.1649 |

Fig. 9

CYSTINE DIAMIDE ANALOGS FOR THE PREVENTION OF CYSTINE STONE FORMATION IN CYSTINURIA

CROSS-REFERENCE AND RELATED APPLICATION

This application claims priority under 35 U.S.C. § 119 (e) to the U.S. Provisional Patent Application 61/748,323 filed on Jan. 2, 2013, the content and teachings of which are incorporated herein by reference in its entirety.

FIELD OF THE INVENTION

The present invention relates to novel cystine analogs, methods of making cystine analogs, compositions containing cystine analogs and methods of using such analogs for inhibiting cystine stone formation and treatment of cystinuria. The cystine analogs of the present invention improve the aqueous solubility of L-cystine in vivo. The present invention also pertains to pharmaceutical compositions comprising these novel compounds for both diagnostic applications and treatment of pathological cystinuria.

BACKGROUND OF THE INVENTION

Cystinuria is a rare chronic lifelong condition that affects about 20,000 Americans. It is the result of an autosomal recessive disorder caused by mutations in one of the two genes, either SLC31A or SLC7A9, leading to abnormal transport of dibasic amino acids from the luminal fluid of the renal proximal tubules and small intestine. About 5% of American women and 12% of American men will develop a kidney stone at some time in their lifetime, and prevalence has been rising in both sexes.

Kidney stone recurrence is also common. It is estimated that almost 50% of stone formers will have a recurrence within 10 years. Approximately 59% of kidney stones are calcium oxalate stones (pure) or with small amounts of calcium phosphate; 10% are predominantly calcium phosphate stones; 17% are uric acid stones; 12% are struvite or infection stones; and remaining 2% are cystine and other stones. Although the rate of cystine stones is much lower than calcium oxalate stones, cystine stones are larger, recur more frequently, and are more likely to cause chronic kidney disease. Medically, the disease caused by cystine stones in the kidney, ureter, and bladder is named cystinuria, which is a genetic abnormality results in abnormal transport of dibasic amino acids from the luminal fluid of the renal proximal tubules and small intestine.

Cystinuria is a chronic, lifelong condition and is most common in young adults under age 40. It is the result of an autosomal recessive disorder caused by mutations in one of the two genes, either SLC3A1 on chromosome 2 (type A) or SLC7A9 on chromosome 19 (type B), which code for components of the major proximal renal tubule cystine and dibasic amino acid transporter. Current clinical treatment of cystinuria aims to reduce the concentration of free cystine in urine and to increase its solubility. A high fluid intake of around 4-5 liters a day and alkalinization of urine pH with citrate or bicarbonate salt can suppress but may not completely prevent stone formation. At severe condition, chelation therapy is necessary, which utilizing the reaction of D-penicillamine or α-mercaptopropionylglycine with L-cystine to generate more soluble asymmetric disulfides. These drugs have side effects including loss of taste, fever, proteinuria, serum sickness-type reactions, and even frank nephritic syndrome.

Recently, a group of researchers reported an alternative approach to prevent cystinuria based on crystal growth inhibition, which is achieved through the binding of tailored growth inhibitors-L-cystine dimethylester (CDME) and L-cystine methylester (CME) to specific crystal surfaces. Real-time in situ atomic force microscopy (AFM) reveals that CDME and CME dramatically reduce the growth velocity of six symmetry-equivalent {100} steps because of specific binding at the crystal surface, which frustrates the attachment of L-cystine molecules. CDME almost completely inhibits the crystallization of L-cystine in water with concentrations above 2 mg/L. While in cell culture experiments, CDME causes loss of cell viability at approximately 1 mM, and in rats study, demonstrates adverse effects at dosages of approximately 500 mg/kg per day.

Even though CDME inhibits cystine stone formation in the in vitro study, the methyl esters in CDME are cleavable by the variety of esterases widely present in almost all organs and tissues, most abundantly in our digestive system, blood and liver. In addition, the ester-mediated hydrolysis of cystine esters will produce cystine, which would add to the already elevated levels of cystine in the kidneys and bladder and potentially increase the likelihood of cystine crystal formation and thus making the problem even worse. Therefore, there is a need for new and improved methods for treating cystinuria.

SUMMARY OF THE INVENTION

The present invention addresses the shortcomings in the prior art including those outlined above by providing cystine analog compounds with enhanced ability to inhibit cystine crystal formations. The present invention provides new cystine analog compounds, methods of synthesizing such compounds, methods of evaluating stable analogs of cystine for inhibition cystine stone formation and methods for treating cystinuria.

In a first aspect, the present invention relates to diamide analogs of L-cystine, and pharmaceutically acceptable salts, solvates, prodrugs and tautomers thereof. In this aspect of the invention, the cystine analog compounds have the structure according to formula (A):

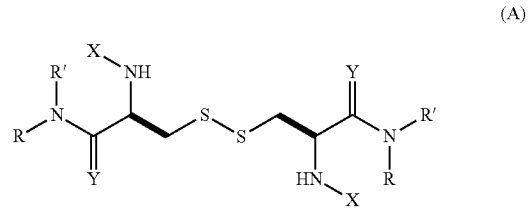

(A)

wherein each R and R' pair are independently selected from (i) or (ii):
  (i) R and R' are independently selected from hydrogen, substituted or unsubstituted alkyl, substituted or unsubstituted alkenyl substituted or unsubstituted alcohol, substituted or unsubstituted aryl, substituted or unsubstituted cycloalkyl, substituted or unsubstituted heterocyclic, substituted or unsubstituted heteroaryl, and
  (ii) R and R' together form a substituted or unsubstituted heterocyclic, or a substituted or unsubstituted heteroaryl;

X is hydrogen, an alkyl, lower alcohol, and Y is O or S.

In one embodiment, with respect to formula (A), X is hydrogen and Y is O.

In one embodiment, with respect to formula (A), at least one R and R' pair together form a substituted or unsubstituted heterocyclic, or a substituted or unsubstituted heteroaryl.

In at least another embodiment at least one R and R' pair together form a ring structure having the formula (B):

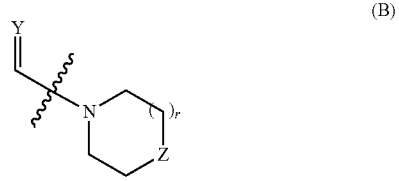

wherein Z is CR"-Q, N-Q or O; and Q and R" are independently selected from hydrogen, substituted or unsubstituted alkyl, substituted or unsubstituted alkenyl, substituted or unsubstituted aryl, substituted or unsubstituted heteroaryl, substituted or unsubstituted cycloalkyl, and substituted or unsubstituted cycloalkenyl, and r is 0-4.

In at least another embodiment, the structure (B) is selected from:

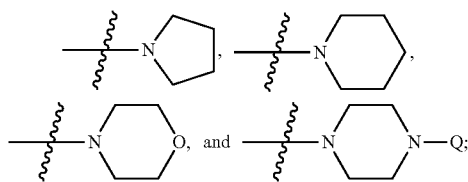

and Q is as defined above. In a preferred embodiment, the formed ring structure is morpholine or piperazine.

In another aspect of the present invention, conjugates of formula (A) are prepared in the form of prodrugs designed to release one or more of such compounds. In a preferred embodiment, the prodrugs of the present compounds have improved oral bioavailability and/or exhibit slower drug release in vivo.

In another embodiment, the disulfide bond is replaced by a linker including substituted or unsubstituted lower alkylene chains such as ethylene (—$CH_2CH_2$—), propylene (—$CH_2CH_2CH_2$—), methyleneoxy (—$CH_2O$—), ethyleneoxy (—$CH_2CH_2O$—), methyleneoxymethyl (—$CH_2OCH_2$—), methylenedioxy (—$OCH_2O$—), methylenesulfenyl (—$CH_2S$—), ethylenesulfenyl (—$CH_2CH_2S$—), methylenesulfenylmethyl (—$CH_2SCH_2$—), or like cycloalkyl rings such as 1,4-cyclohexyl, 1,3-cyclopentyl, or like substituted cycloalkyl rings such as tetrahydropyran-2,5-diyl, tetrahydrofuran-2,5-diyl, tetrahydrothiophen-2,5-diyl, or substituted or unsubstituted aryl or heteroaryl rings.

Another aspect of the invention provides a pharmaceutical composition for inhibiting the formation of cystine kidney stone or slowing the growth of L-cystine crystallization comprising a pharmaceutically acceptable carrier and a pharmaceutically effective amount of a compound according to formula (A).

Yet another aspect of the invention provides a method for treating, inhibiting or retarding the growth of L-cystine kidney-stone formation in a subject in need thereof, the method comprising administering to the subject a pharmaceutically effective amount of a compound according to formula (A).

In yet another aspect of the invention provides a method of treating a subject having cystinuria, comprising administering to the subject in need of such treatment a pharmaceutically effective amount of a compound according to formula (A).

In a further aspect, the present invention provides pharmaceutical compositions, comprising a compound or compounds of the invention in combination with other modalities known in the art for treatment of cystinuria, an acceptable pharmaceutical carrier, excipient or diluent. In this aspect of the invention, pharmaceutical composition can comprise one or more of the analog compounds described herein.

BRIEF DESCRIPTION OF THE DRAWINGS

FIG. 4 provides a summary of effects of the novel compounds on cystine solubility.

FIG. 8 provides the table showing the volume of urine collected before and after treatment with LH707 and LH708.

FIG. 9 provides urine amino acid concentration upon a four-week treatment with LH708. Accordingly, cystine was the only amino acid that has significantly increased upon treatment with LH708 using the conventional criteria of statistical significance in paired t-test.

DETAILED DESCRIPTION OF THE INVENTION

Definitions

Figure 1:
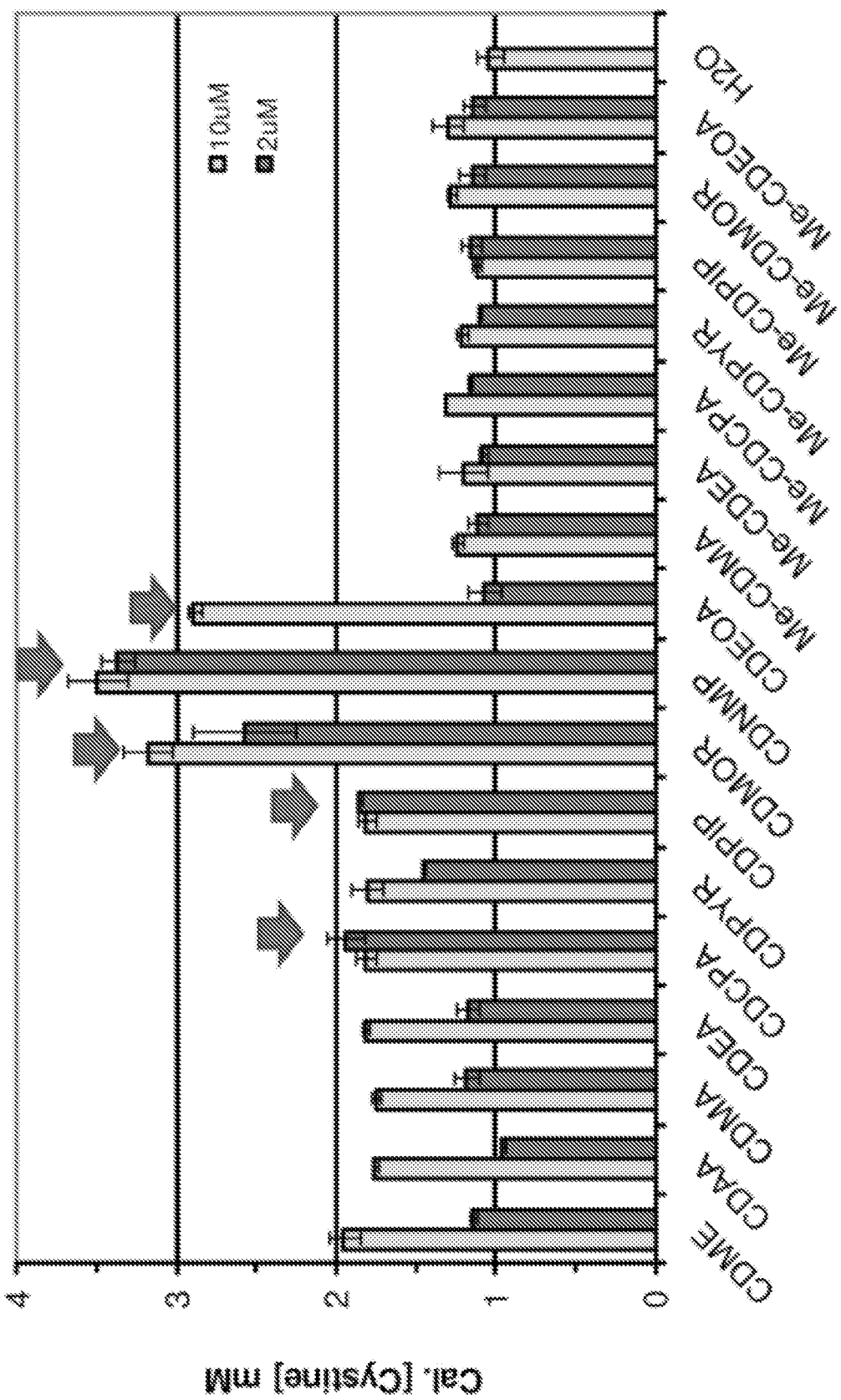
FIG. 1 is a depiction of the effect of L-cystine diamindes on the solubility of L-cystine in water and as compared to CDME.

When describing the compounds, pharmaceutical compositions containing such compounds and methods of using such compounds and compositions, the following terms having the following meanings unless otherwise indicated. It should also be understood that any of the moieties defined forth below may be substituted with a variety of substituents and that the respective definitions are intended to include such substituted moieties within their scope.

"Alkyl" refers to monovalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms.

"Alkylene" refers to divalent saturated alkene radical groups having 1 to 18 carbon atoms and more particularly 1 to 6 carbon atoms which can be straight-chained or branched. This term is exemplified by groups such as methylene (—CH$_2$—), ethylene (—CH$_2$CH$_2$—), and the like.

"Substituted alkyl" includes those groups recited in the definition of "substituted" herein, and particularly refers to an alkyl group having 1 or more substituents, for instance from 1 to 5 substituents, and particularly from 1 to 3 substituents, selected from acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioakoxy, thioaryloxy, thioketo, thiol, alkyl-S(O)—, aryl-S(O)—, and alkyl-S(O)$_2$—.

Substituted alkylene" includes those groups recited in the definition of "substituted" herein, and particularly refers to an alkylene group having 1 or more substituents, for instance from 1 to 5 substituents, and particularly from 1 to 3 substituents, selected from acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, and alkyl-S(O)$_2$.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acephenanthrylene, anthracene, azulene, benzene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, and the like. Particularly, an aryl group comprises from 6 to 14 carbon atoms.

Substituted "Aryl" includes those groups recited in the definition of "substituted" herein, and particularly refers to an aryl group that may optionally be substituted with 1 or more substituents, for instance from 1 to 5 substituents, particularly 1 to 3 substituents, selected from acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, and alkyl-S(O)$_2$.

"Amino" refers to the radical —NH$_2$.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methyl-cyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)— and alkyl-S(O)$_2$.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloheteroalkyl.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, carbazole, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred.

"Pharmaceutically acceptable" means approved by a regulatory agency of the Federal or a state government or listed in the U.S. Pharmacopoeia or other generally recognized pharmacopoeia for use in animals, and more particularly in humans. As noted herein, the salts of the compounds of this invention refer to non-toxic "pharmaceutically acceptable salts." Other salts may, however, be useful in the preparation of the compounds according to the invention or of their pharmaceutically acceptable salts.

"Pharmaceutically acceptable carrier" refers to a diluent, adjuvant, excipient or vehicle with which a compound of the invention is administered.

"Prodrugs" refers to compounds, including derivatives of the compounds of the invention, which have cleavable groups which respectively cleave under physiological conditions and form pharmaceutically active form of the present compounds in vivo. Such examples include, but are not limited to, lower and long alkyl ester derivatives and the like, choline and N-alkylmorpholine esters and the like. Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. In some cases it is desirable to prepare double ester type prodrugs such as (acyloxy)alkyl esters or ((alkoxycarbonyl)oxy)alkylesters.

"Solvate" refers to forms of the compound that are associated with a solvent. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Tautomers" refer to compounds that are interchangeable forms of a particular compound structure, and that vary in the displacement of hydrogen atoms and electrons. Thus, two structures may be in equilibrium through the movement of .pi. electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or composition of the invention for cosmetic purposes. "Prophylactic treatment" is to be construed as any mode of treatment that is used to prevent progression of the disease or is used for precautionary purpose for persons at risk of developing the condition.

The compounds of the present invention may possess one or more asymmetric centers; such compounds can therefore be produced as individual (R)- or (S)-stereoisomers or as mixtures thereof.

As used herein, the $EC_{2x}$'s are the concentrations required of the candidate compounds to double the aqueous solubility of cystine and were determined to assess drug potency and potential dosing regimens for in vivo use. One of ordinary skill in the art is readily able to ascertain such information using commonly known methodologies.

For purposes of treating cystinuria in a mammalian subject, such as a human patient, an effective amount of one or more compounds of the present invention, or a pharmaceutically-acceptable salt thereof, is administered to the subject to improve the solubility of cystine and prevent the formation or reduce the rate of growth of a cystine crystals and kidney stones.

As discussed herein, the cystine analog compounds of the present invention can be administered in oral dosage forms such as tablets, capsules (each of which includes sustained release or timed release formulations), pills, powders, micronized compositions, granules, elixirs, tinctures, suspensions, syrups and emulsions. Likewise, they may also be administered in intravenous (bolus or infusion), subcutaneous, intramuscular form, or other forms well known to those of ordinary skill in the pharmaceutical arts. For example, intramuscular injection of a depot formulation containing lipophilic prodrugs in the form of long alkyl ester derivatives of the cystine analog compounds maybe used to slowly release the active cystine analog compounds for long-term management of cystinuria. The ordinary skilled physician, veterinarian or clinician can readily determine and prescribe the effective amount of the drug required to prevent, counter or arrest the progress of the condition. Effective dosage forms, modes of administration and dosage amounts may be determined empirically and will vary with the activity of the particular compound employed, course and/or progression of the disease state, the route of administration, the rate of excretion of the compound, renal and hepatic function of the patient, the duration of the treatment, the identity of any other drugs being administered to the subject, age, size and like factors well known in the medical arts.

Pharmaceutical formulations of the present invention include those suitable for oral, rectal, and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the active ingredient(s).

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethylacetate, butyl alcohol, benzyl benzoate, propylene glycol, glycol, oils (in particular, cottonseed, groundnut, corn, germ, olive, castor and sesame oils), glycerol, amyl alcohol, tetrahydrofuryl polyethylene glycols and fatty acid esters of sorbitan, and mixtures thereof.

Besides inert diluents the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated alcohols, polyoxyethylene sorbitol and sorbitan esters, microcrystalline cellulose, aluminum metahydroxide, bentonite, agar-agar and tragacanth, and mixtures thereof.

Oral dosages of the present invention, when used for the indicated effects, will range between about 0.01 mg per kg of body weight per day (mg/kg/day) to about 5000 mg/kg/day, preferably 0.1 to 2500 mg/kg/day, and most preferably 10 to 1500.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 500 and 1000 milligrams of the cystine diamide analog compounds of the present invention ingredient for the symptomatic adjustment of the dosage to the patient to be treated.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions of this invention suitable for parenteral administration comprise the active ingredient(s) or prodrug form(s) in combination with one or more pharmaceutically-acceptable sterile isotonic aqueous or nonaqueous solutions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Injectable depot forms are made by forming microencapsule matrices of the active ingredient(s) or prodrug form(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

Another aspect of the present invention is directed to methods of treating a subject diagnosed with cystinuria by administering to said subject a pharmaceutically effective amount of the presently disclosed compounds. As noted herein, the cystine analog compounds of the present invention can be used in combination with other agents used for treatment of cystinuria or other agents which will enhance such treatment regime for subjects in need of such treatment. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly. It will be understood that the scope of combinations of the compounds of this invention with other agents useful to treat the targeted condition includes in principle any combination with any pharmaceutical composition useful for treating disorders related to kidney stone or related chronic kidney disease.

In at least one aspect of the present invention, it is more convenient or desirable to prepare, purify, and/or handle the active compound in the form of a prodrug. The term "prodrug" as used herein, pertains to a compound which, when metabolized, yields the desired active compound or in itself is the active compound. This includes for example adding a phosphoric acid ester moiety, alkoxycarbonyl (ROCO), (acyloxy)alkoxycarbonyl (RCOOCH(R') OCO, where R and R' are the same as above; in suitable positions such as positions X or Q in formulas A and B. Typically, the prodrug is inactive, or less active than the active compound, but may provide advantageous handling, administration, or metabolic properties.

Various cystine diamide analogs in accordance with this invention would be understood by those skilled in the art made aware of this invention, as available through synthetic procedures of the sort described herein or straight-forward modifications thereof.

At least one aspect of the present invention provides for methods of synthesizing the present compounds and further preparing suitable formulations. In at least one embodiment, the method of synthesizing cysteine diamide analog follows the steps of: (i) obtaining N-alkyl cysteine by reducing thiazolidine-4-carboxylic acid; (ii) producing N, N' dialkyl cysteine by oxidizing the N-alkyl cysteine of step (i) in the presence of suitable transitional metal catalytic compound; (iii) protecting the secondary amine with Boc anhydride, and amidation through activated ester; and (iv) deprotecting the target N,N'-substituted L-cystine.

In more specific embodiment, the compounds of the present invention can be synthesized by the following methods as depicted in the schemes below:

Scheme 1 provides the making of compounds I-IX through the amidation of L-cystine using activated OSu or OBt ester and subsequent deprotection of Boc group using 50% TFA in $CH_2Cl_2$ or 4 equiv. of 4 N HCl in dioxane. Amidation using activated esters was found to give better reaction yields and fewer side products. The total yields of the three step sequence ranged from 10% to 50%.

Scheme 1. The synthesis of compounds I-IX starting from L-cystine.

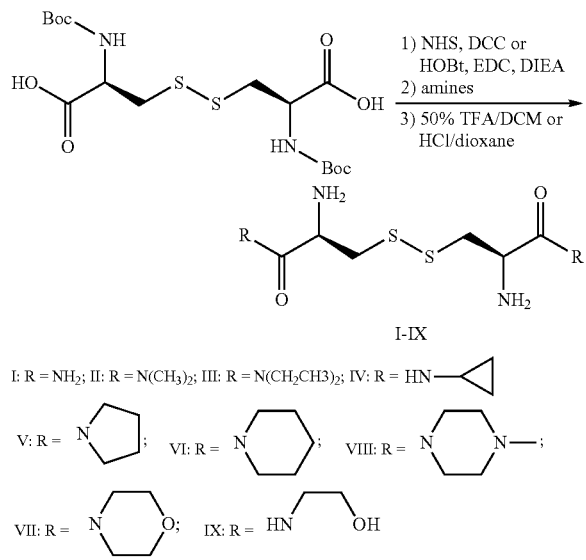

Several conditions were initially used to direct methylate L-cystine but failed to obtain N,N'-dimethyl L-cystine. The process was thus modified according to Scheme 2 to first obtain N-methyl cysteine through Na—$NH_3$ reduction of thiazolidine-4-carboxylic acid and then air oxidize the N-methyl cysteine in the presence of catalytic iron (III) chloride to afford the desired N,N'-dimethyl L-cystine. Protection of the secondary amine with Boc anhydride, amidation through activated ester and subsequent deprotection afford the target N,N'-dimethyl L-cystine amides X-XVI in 10% to 30% overall yield Scheme 2. The synthesis of N-methyl analogs X-XVI.

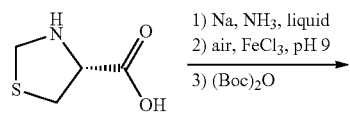

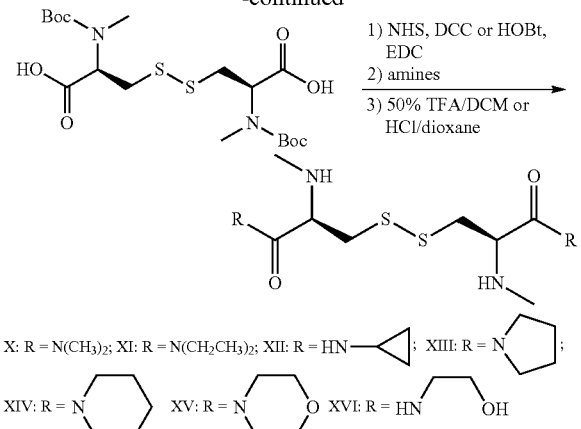

As described herein, the cystine analogs of the present invention have the structure formula (A):

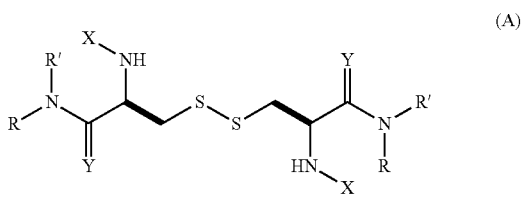

wherein each R and R' pair are independently selected from (i) or (ii)

(i) R and R' are independently selected from hydrogen, substituted or unsubstituted alkyl, substituted or unsubstituted alkenyl, substituted or unsubstituted alcohol, substituted or unsubstituted aryl, substituted or unsubstituted cycloalkyl, substituted or unsubstituted heterocyclic, substituted or unsubstituted heteroaryl, and (ii) R and R' together form a substituted or unsubstituted heterocyclic ring structure, or a substituted or unsubstituted heteroaryl ring structure; and X is hydrogen, an alkyl, lower alcohol, and Y is O or S.

In one embodiment, at least one R and R' pair together form a ring structure having the formula (B):

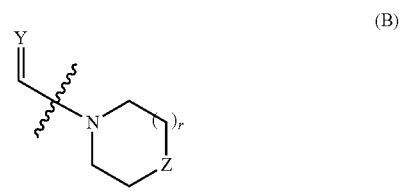

wherein Z is CR"-Q, N-Q or U; and Q and R" are independently selected from hydrogen, substituted or unsubstituted alkyl, substituted or unsubstituted alkenyl, substituted or unsubstituted aryl, substituted or unsubstituted heteroaryl, substituted or unsubstituted cycloalkyl, and substituted or unsubstituted cycloalkenyl, and r is 0-4.

In at least another embodiment, the structure (B) is selected from:

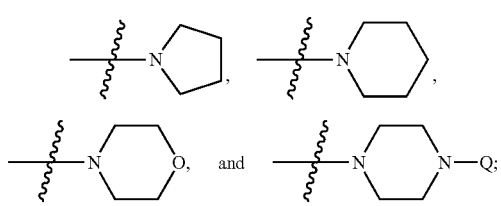
and Q is as defined above. In a preferred embodiment the formed ring is morpholine or piperazine.
In at least one embodiment with respect to formula (A), the cystine analog compound having the structures according to the following formulas:
(I)
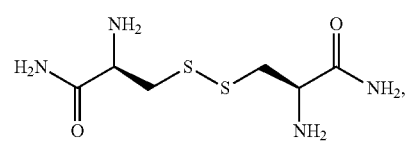
(II)
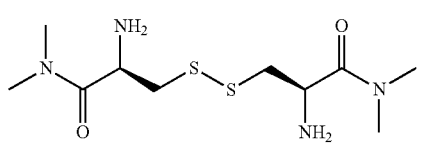
(III)
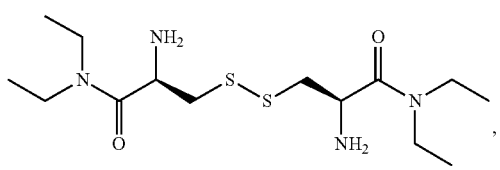
(IV)
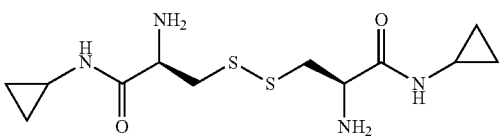
(V)
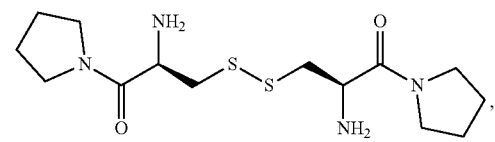
(VI)
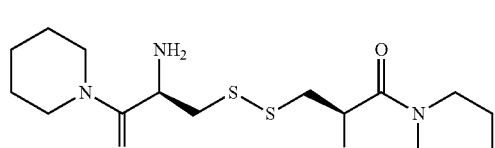
(VII)
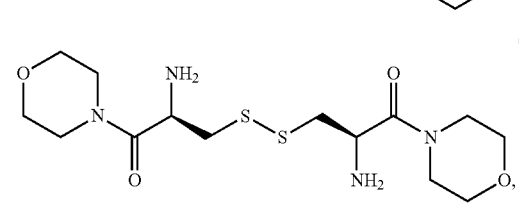
-continued
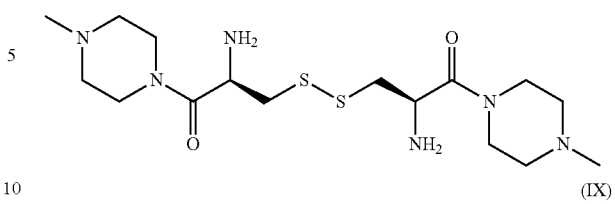
(VIII)
(IX)
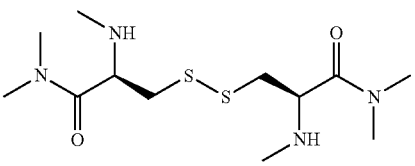
(X)
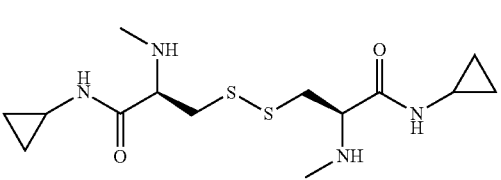
(XI)
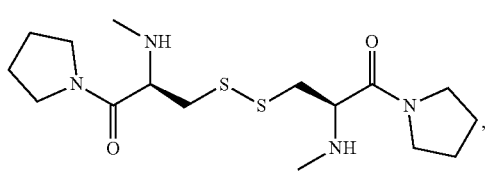
(XII)
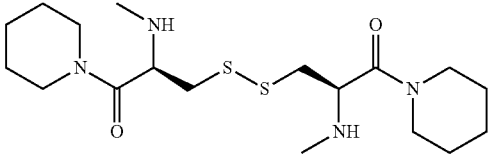
(XIII)
(XIV)
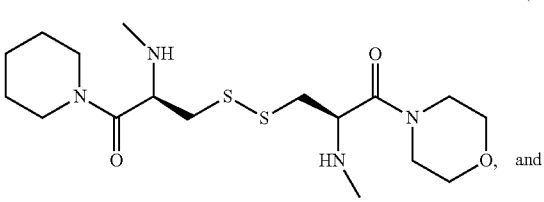
(XV)
and -continued (XVI)

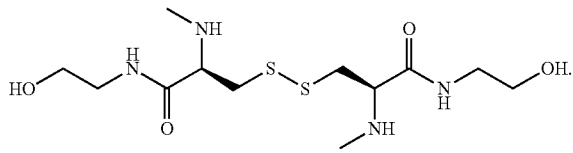

In a more preferred embodiment the compounds have a structure according to the following formulas:

(VII)

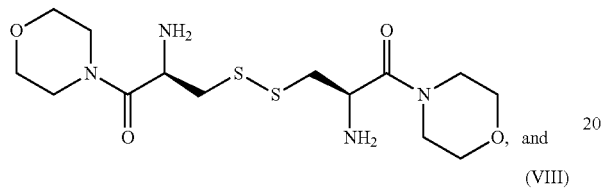

and (VIII)

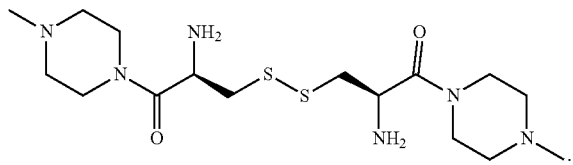

At least one aspect of the present invention is to provide series of cystine diamides that increases the aqueous solubility of L-cystine. In at least one embodiment, the cysteine concentration in urine of a subject receiving the cysteine diamide increases by at least 30%, 40%, 50%, 60%, 70%, 80%, 90%, 95%, 98%, 99%. In a preferred embodiment, the urine concentration of cysteine is increased by at least 70%, while the concentration of other urine amino acids-remains statistically unchanged after the completion of the treatment regimen.

Another aspect of the present invention introduces cystine diamides that exhibits a 1-1000 fold increase in potency as compared to those available in the prior art. At least in another embodiment the compounds of the present invention show an increase in potency by 7 to 50 folds. At least two compounds of the present invention exhibited at least a 7 and a 24 fold increase in potency as compared to the control CDME. The present compounds having the formulas VII and VIII respectively showed a 7.44 and 24.41 fold increase in activity as compared to CDME.

In at least another aspect of the present invention, a prodrug conjugate is designed according to the structure of formula (C):

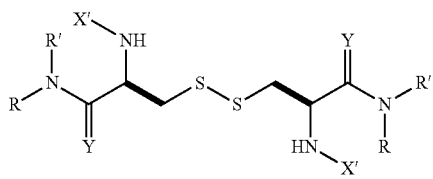

wherein each R and R' pair are independently selected from (i) or (ii):
(i) R and R' are independently selected from hydrogen, substituted or unsubstituted alkyl, substituted or unsubstituted alkenyl, substituted or unsubstituted alcohol, substituted or unsubstituted aryl, substituted or unsubstituted cycloalkyl, substituted or unsubstituted heterocyclic, substituted or unsubstituted heteroaryl, and
(ii) R and R' together form a substituted or unsubstituted heterocyclic ring structure, or a substituted or unsubstituted heteroaryl ring structure:
Y is O or S; and X' is selected from alkoxycarbonyl (ROCO), (acyloxy)alkoxycarbonyl (RCOOCH(R')OCO, where R and R' are the same as above.

In at least another embodiment of this aspect of the invention, at least one of the R and R' of die prodrug conjugate form a ring structure having the formula (D):

(D)

wherein Z' is CR"—W, N—W or O; and R" is selected from hydrogen, substituted or unsubstituted alkyl, substituted or unsubstituted alkenyl, substituted or unsubstituted aryl, substituted or unsubstituted heteroaryl, substituted or unsubstituted cycloalkyl, and substituted or unsubstituted cycloalkenyl, and W is selected from alkoxycarbonyl (ROCO), (acyloxy)alkoxycarbonyl (RCOOCH(R')OCO, where R and R' are the same as above; and r is 0-4.

As set forth herein the prodrugs of the disclosed compounds are designed to release one or more of such compounds. In yet another embodiment, the prodrug has the general formula of (C) and (D) as above, wherein X' and/or W is selected from alkoxycarbonyl (ROCO), (acyloxy) alkoxycarbonyl (RCOOCH(R')OCO, R and R' are the same as above.

In another embodiment, the disulfide bond is replaced by a linker. Accordingly, the cystine analogs of the present invention can have the structure formula (E):

(E)

wherein each T and T' pair are independently selected from (i) or (ii):
(i) T and T' are independently selected from hydrogen, substituted or unsubstituted alkyl, substituted or unsubstituted alkenyl, substituted or unsubstituted alcohol, substituted or unsubstituted aryl, substituted or unsubstituted cycloalkyl, substituted or unsubstituted heterocyclic, substituted or unsubstituted heteroaryl, and
(ii) T and T' together form a substituted or unsubstituted heterocyclic ring structure, or a substituted or unsubstituted heteroaryl ring structure;
X" is hydrogen, an alkyl, lower alcohol, and Y" is O or S; and L is a linker selected from a group consisting of substituted or unsubstituted lower alkylene chains such as ethylene (—CH$_2$CH$_2$—), propylene (—CH$_2$CH$_2$CH$_2$—), methyleneoxy (—CH$_2$O—), ethyleneoxy (—CH$_2$CH$_2$O—), methyleneoxymethyl (—CH$_2$OCH$_2$—), methylenedioxy (—OCH$_2$O—), methylenesulfenyl (—CH$_2$S—), ethylenesulfenyl (—CH$_2$CH$_2$S—), methylenesulfenylmethyl (—CH$_2$SCH$_2$—), or substituted or unsubstituted cycloalkyl rings such as 1,4-cyclohexyl, 1,3-cyclopentyl tetrahydropyran-2,5-diyl tetrahydrofuran-2,5-diyl, tetrahydrothiophen-2,5-diyl, or substituted or unsubstituted aryl or heteroaryl rings.

In one embodiment, at least one T and T' pair together form a ring structure having the formula (F):

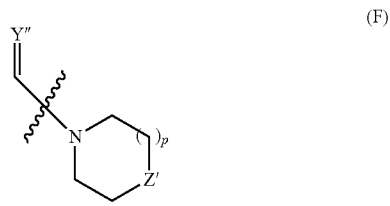

wherein Z' is CT"-Q', N-Q' or O; and Q' and T" are independently selected from hydrogen, substituted or unsubstituted alkyl, substituted or unsubstituted alkenyl, substituted or unsubstituted aryl, substituted or unsubstituted heteroaryl, substituted or unsubstituted cycloalkyl, and substituted or unsubstituted cycloalkenyl, and p is 0-4.

In at least another embodiment, the structure (F) is selected from:

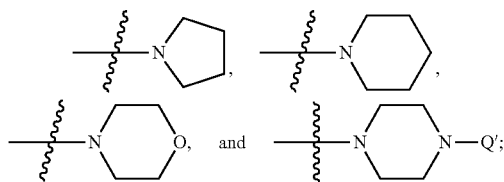

and Q' is as defined above. In a preferred embodiment the formed ring is morpholine or piperazine.

The general methods given in Schemes 1 and 2 for the preparation of cystine analog compounds disclosed here and further in Table 1. The preferred cystine analog compounds of the present invention are further illustrated by the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

EXAMPLES

Example 1—Experimental Synthesis of L-Cystine Diamides (I-IX)

NHS (1.7 g, 15.0 mmol) and DCC (3.1 g, 15.0 mmol) were added the solution of N,N'-bis(tert-butoxycarbonyl)-L-cystine (3.0 g, 6.8 mmol) in ethyl acetate (200 mL), and the mixture was stirred at r.t. for 2 hr. After the filtration, the liquid was concentrated and dissolved in anhydrous DCM. After filtration to remove the DCU precipitates, the solvent was removed under reduced pressure to give the crude activated ester as a white solid (2.1 g, 48.6%), which was used without further purification. Similarly, HOBt and EDC can be used to prepare N,N'-Bis(tert-butoxycarbonyl)-L-cystine OBt ester for reaction with amines.

The activated esters of N,N'-Bis(tert-butoxycarbonyl)-L-cystine were dissolved in a suitable solvent such as acetonitrile, methylene chloride, DMF or NMP. To the solution of an activated ester of N,N'-Bis(tert-butoxycarbonyl)-L-cystine, excess amine (3-10 eq) was added and the reaction was allowed to proceed at r.t. for 2 hr. At the end of reaction as monitored by LC-MS or TLC, solvent was removed under reduced pressure and the residue was dissolved in DCM and washed with Millipore water for 3 times. After concentration, the crude product was purified by ISCO (normal phase, DCM-20% MeOH/DCM). The purified oil was dissolved into 50% TFA/DCM and stirred for 1 hr to remove the Boc protecting group. After TFA and DCM were removed by N$_2$, diethyl ether was used to precipitate desired product. After centrifuge, the solid was collected and dissolved into Millipore water, and washed with ethyl acetate for 3 times. The aqueous solution was lyophilized to final product. To obtain the HCl salt of L-cystine diamides, deprotection of Boc-cystine diamides was performed using 4 N HCl in dioxane (4 equiv).

L-Cystine diamide (CDAA, LH701, I): 8.1 mg (71.9% yield). LC-MS (ESI+) m/z 238.9 [M+H]$^+$; 1H-NMR (400 MHz, D$_2$O, δ): 4.24 (dd, 2H), 3.28 (dd, 2H), 3.07 (dd, 2H).

L-Cystine bis(dimethylamide) (CDMA, LH702, II): 4.2 mg (30.2% yield). LC-MS (ESI+) m/z 294.9 [M+H]$^+$; 1H-NMR (400 MHz, D$_2$O, δ): 4.78 (m, 2H), 3.30 (dd, 2H), 3.12 (dd, 2H), 3.10 (s, 6H), 2.93 (s, 6H).

L-Cystine bis(diethylamide) (CDEA, LH703, III): 3.7 mg (22.3% yield). LC-MS (ESI+) m/z 350.8 [M+H]$^+$; 1H-NMR (400 MHz, D$_2$O, δ): 4.78 (m, 2H), 3.46 (m, 6H), 3.29 (m, 4H), 3.20 (m, 2H), 1.20 (t, 6H), 1.09 (t, 6H).

L-Cystine bis(cyclopropylamide) (CDCPA, LH704, IV): 8.6 mg (57.2% yield). LC-MS (ESI+) m/z 318.8 [M+H]$^+$; 1H-NMR (400 MHz, D$_2$O, δ): 4.13 (t, 2H), 3.20 (dd, 2H), 3.11 (dd, 2H), 2.57 (p, 2H), 0.72 (m, 4H), 0.50 (m, 4H).

L-Cystine bis(pyrrolidine) (CDPYR, LH705, V): 12.6 mg (76.9% yield). LC-MS (ESI+) m/z 346.9 [M+H]$^+$; 1H-NMR (400 MHz, D$_2$O, δ): 4.57 (dd, 2H), 3.61 (m, 2H), 3.54 (m, 2H), 3.46 (m, 2H), 3.36 (m, 2H), 3.29 (dd, 2H), 3.14 (dd, 2H), 1.95 (m, 4H), 1.86 (m, 4H).

L-Cystine bispiperidine (CDPIP, LH706, VI): 11.5 mg (65.0% yield). LC-MS (ESI+) mu/z 374.8 [M+H]$^+$; 1H-NMR (400 MHz, D$_2$O, δ): 4.78 (m, 2H), 3.46 (t, 8H), 3.16 (m, 4H), 1.57 (m, 6H), 1.50 (m, 6H).

L-Cystine bis(N'-methylpiperazide) (CDNMP, LH708, VIII): 12.8 mg (67.0% yield). LC-MS (ESI+) m/z 404.9 [M+H]$^+$; 1H-NMR (400 MHz, D$_2$O, δ): 4.76 (m, 2H), 3.56-3.78 (m, 22H), 3.24 (m, 4H).

L-Cystine bismorpholide (CDMOR, LH707, VII): 10.2 mg (57.0% yield). LC-MS (ESI+) m/z 378.8 [M+H]$^+$; 1H-NMR (400 MHz, D$_2$O, δ): 4.80 (t, 2H), 3.60-3.76 (m, 16H), 3.25 (m, 4H).

L-Cystine diethanolamide (CDEOA, LH709, IX): 6.3 mg (40.8% yield). LC-MS (ESI+) m/z 326.8 [M+H]$^+$; 1H-NMR (400 MHz, D$_2$O, δ): 4.18 (t, 2H), 3.66 (t, 4H), 3.24 (m, 6H), 2.99 (m, 2H).

Example 2—Synthesis of N,N'-dimethyl L-Cystine Diamides (X-XVI)

Thiazolidine-4-carboxylic acid (6.66 g, 50 mmol) was dissolved in 60 mL of liquid ammonia at −78° C., to which was added H$_2$O (0.9 mL). Solid sodium was added until the solution remained blue (~3.8 g). The reaction was quenched with the addition of NH$_4$Cl (11 g, 205.6 mmol), after which the mixture was allowed to warm to room temperature and evaporate overnight. After drying under vacuum, the crude white solid was dissolved in 50 mL of water and acidified to pH 1 with 6 N HCl. The solvent and excess acid were removed under reduced pressure to reveal a sticky off-white solid. The solid was extracted with absolute EtOH, which yielded a sticky yellow solid after removal of the solvent. The N-methylated cysteine was air-oxidized to the disulfide by dissolving in 250 mL of water, at pH 9 (adjusted with ammonium hydroxide), in presence of iron (III) chloride (1 crystal) and bubbling with air overnight. After 13 h, the solution tested negative for thiolates using the nitroprusside reaction. The solution was acidified to pH 6 with 25% AcOH. Addition of 100 mL of absolute EtOH precipitated a thick white solid which was removed by centrifugation and washed twice with 50% EtOH. The solid was dissolved in water and lyophilized yielding 4.3 g (32.1% yield) of N,N'-dimethyl cystine as fluffy off-white solid. LC-MS (ESI+): m/z 268.7 [M+H]$^+$.

To a stirred solution of N,N'-dimethyl L-cystine (2.5 g, 9.32 mmol) in sodium bicarbonate solution (50 mL) at 0° C., was added di-tert-butyl dicarbonate (6.0 g, 27.4 mmol) in acetone (10 mL) dropwise over the course of approximately 2 hr. The reaction was stirred overnight and allowed to slowly warm to r.t. The pH of reaction mixture was adjusted to 5 using 5% sodium bisulfate solution The mixture was extracted with ethyl acetate (3×100 mL). The combined organic layers were dried over Na$_2$SO$_4$ and concentrated in vacuo. The residue was purified by column chromatography on silica gel to yield 2.3 g (51.8% yield) of N,N'-Bis(tert-butoxycarbonyl)-N,N'-dimethyl L-cystine. LC-MS (ESI+): m/z 468.9 [M+H]$^+$.

The N,N'-dimethyl L-cystine diamides (X-XVI) were prepared in a similar fashion as above by activating N,N'-Bis(tert-butoxycarbonyl)-N,N'-dimethyl L-cystine with HOSu/DCC or HOBt/EDC, subsequently reacting the activated esters with excess amines, and final deprotection with 50% TFA/CH$_2$Cl$_2$ or 4 N HCl in dioxane.

N,N'-Dimethyl L-cystine bis(dimethylamide) (Me-CDMA, LH710, X): 6.2 mg (42.5% yield). LC-MS (ESI+) m/z 322.9 [M+H]$^+$; 1H-NMR (400 MHz, D$_2$O, δ): 4.70 (m, 2H), 3.30 (t, 4H), 3.11 (s, 6H), 2.95 (s, 6H), 2.67 (s, 6H).

N,N'-Dimethyl L-cystine bis(diethylamide) (Me-CDEA, LH711, XI): 2.3 mg (13.4% yield). LC-MS (ESI+) m/z 378.8 [M+H]$^+$; 1H-NMR (400 MHz, D$_2$O, δ): 4.60 (m, 2H), 3.29-3.50 (m, 12H), 2.68 (s, 6H), 1.21 (t, 6H), 1.11 (t, 6H).

N,N'-Dimethyl L-cystine bis(cyclopropylamide) (Me-CDCPA, LH712, XII): 8.8 mg (56.1% yield). LC-MS (ESI+) m/z 346.8 [M+H]$^+$; 1H-NMR (400 MHz, D$_2$O, δ): 4.01 (t, 2H), 3.23 (m, 4H), 2.67 (s, 6H), 2.66 (m, 2H), 0.76 (m, 4H), 0.54 (m, 4H).

N,N'-Dimethyl L-cystine bis(pyrrolidine) (Me-CDPYR, LH713, XIII): 7.6 mg (44.7% yield). LC-MS (ESI+) m/z 374.8 [M+H]$^+$; 1H-NMR (400 MHz, D$_2$O, δ): 4.48 (t, 2H), 3.64 (m, 2H), 3.55 (m, 2H), 3.48 (m, 2H), 3.40 (m, 2H), 3.29 (dd, 4H), 2.68 (s, 6H), 1.95 (m, 4H), 1.88 (m, 4H).

N,N'-Dimethyl L-cystine bispiperidine (Me-CDPIP, LH714, XV): 9.4 mg (51.6% yield). LC-MS (ESI+) m/z 402.8 [M+H]$^+$; 1H-NMR (400 MHz, D$_2$O, δ): 4.78 (m, 2H), 3.52 (m, 8H), 3.29 (d, 4H), 2.67 (s, 6H), 1.62 (m, 6H), 1.56 (m, 6H).

N,N'-Dimethyl L-cystine bismorpholide (Me-CDMOR, LH715, XV): 5.1 mg (27.7% yield). LC-MS (ESI+) m/z 406.8 [M+H]$^+$; 1H-NMR (400 MHz, D$_2$O, δ): 4.70 (m, 2H), 3.73 (m, 8H), 3.62 (m, 8H), 3.30 (t, 4H), 2.68 (s, 6H).

N,N'-Dimethyl L-cystine diethanolamide (Me-CDEOA, LH716, XVI): 4.8 mg (30.1% yield). LC-MS (ESI+) m/z 354.8 [M+H]$^+$; 1H-NMR (400 MHz, D$_2$O, δ): 4.15 (t, 2H), 3.65 (m, 4H), 3.42 (m, 4H), 3.29 (d, 4H), 2.68 (s, 6H).

Figure 3:
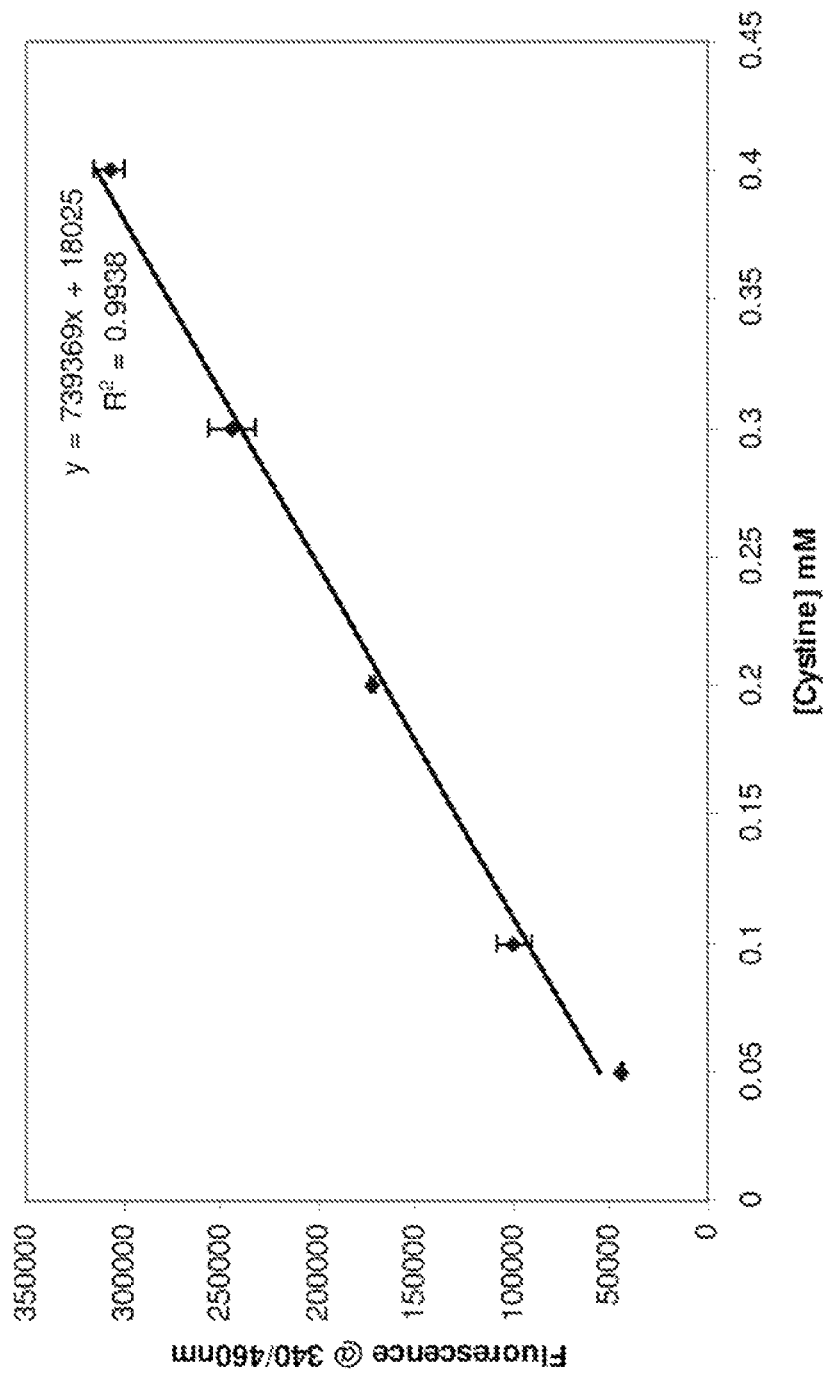
FIG. 3 provides the standard curve of cystine using the OPA method.

Another aspect of the present invention is directed to the processes of determining the concentration of L-cystine using a fluorescence assay after OPA/NBC derivatization. In at least one embodiment with respect to this aspect of the invention, the concentration of the L-cystine was assessed by a fluorescence assay. Accordingly, the inventors developed a fluorescence-based assay using O-phthaldialdehyde (OPA) and N-Boc-cysteine (NBC) to accurately measure the concentration of L-cystine in aqueous solutions using a similar protocol we previously reported. OPA/NBC are popular reagents used for precolumn derivatization of amino acids in HPLC. This derivatization is fast and simple to operate. However, the reaction of OPA with the disulfide cystine and NBC yielded derivatives with weak fluorescence. The disulfide in cystine was reduced and then alkylated with iodoacetic acid to form S-carboxymethylcysteine, which yielded OPA/NBS derivatives with normal fluorescence. L-Cystine solution was thus used to construct a standard curve. L-Cystine first reacted with DTT for 10 min, followed by reaction with iodoacetic acid for 15 min, then reacted with OPA and NBC for 3 min. The final mixture was pipetted into 384-well plate and the fluorescence intensity was read at Ex 340 nm/Em 460 nm. A linear standard curve was obtained in the concentration range between 50 μM and 400 μM (see FIG. 3).

Example 3—Fluorescence Assay for Inhibition of L-Cystine Crystal Formation

Formation of supersaturation solution—a supersaturated solution was formed by dissolving 21 mg of L-cystine in 30 mL of Millipore water (~3 mM) under reflux at 100° C. for 20 min until the L-cystine was completely dissolved. The supersaturated solution was then allowed to cool slowly with stirring for 75 min.

Construction of standard curves—L-Cystine (5 mg) was dissolved in Millipore water (34.7 mL) to form a 0.6 mM solution as a stock solution. Then, L-cystine solution was diluted to 0.4, 0.3, 0.2, 0.1, 0.05 mM solution, 10 uL of each L-cystine solutions, 90 uL of 0.1 M dibasic sodium phosphate solution, and 10 uL of DTT solution (12.5 mM) were mixed at r.t. for 10 min. before the addition of 10 uL of iodoacetic acid (100 mM) and continued incubation at r.t. for an additional 15 min. This was then followed by the addition of 10 uL of OPA (100 mM in methanol) and 10 uL of NBC (100 mM in methanol). The derivatization was allowed to proceed for 3 min before 40 uL of the mixture was plated in a 384-well plate and read at Ex 340 nm/Em 460 nm. The standard curve was repeated for each set of experiments and used to calculate the concentration of L-cystine in each sample.

The mechanism of OPA method for determination of cystine concentration is depicted in the following scheme:

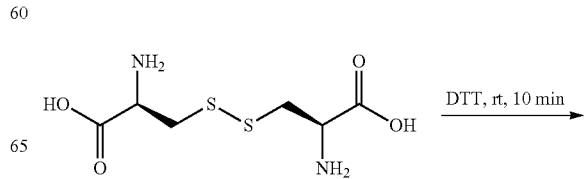

-continued

[Reaction scheme: HS-CH2-CH(NH2)-COOH + Iodoacetic acid, rt, 15 min → HOOC-CH2-S-CH2-CH(NH2)-COOH + OPA/NBC → isoindole fluorescent product]

Blue Fluorescence
(Ex: 340 nm, Em: 460 nm)

Determination of L-cystine concentration—All test compounds were dissolved in water to form 10 mM stock solution, 5 uL of each solution was added to 500 uL L-cystine supersaturated solution. The mixtures were allowed to stand at 25° C. for 72 h. At the end of incubation, the mixtures were centrifuged at 10,000 rpm for 4 min and the supernatants were diluted 2-fold for concentration measurement. Each diluted mixture (10 uL), 0.1 M dibasic sodium phosphate solution (90 uL), and 10 uL of DTT solution (12.5 mM) were mixed at r.t. for 10 min, before the addition of 10 uL of iodoacetic acid (100 mM) and continued incubation at r.t. for an additional 15 min. Derivatization was performed by the addition of 10 uL of OPA (100 mM in methanol) and 10 uL of NBC (100 mM in methanol) for 3 min. 40 uL of the derivatized mixture was plated in a 384-well plate and fluorescence was read at Ex 340 nm/Em 460 nm to derive the concentrations of the original mixtures.

Example 4—Primary Screening of L-Cystine Diamides Synthesized

In order to determine the effects of L-cystine diamides synthesized on the aqueous solubility of L-cystine, a supersaturated solution of L-cystine was prepared in Millipore water according to the literature method. Then, 1 mM and 200 uM solutions of each L-cystine diamide synthesized were added to a supersaturated solution of L-cystine in water (1:100) to give supersaturated solutions of L-cystine containing 10 μM and 2 μM of a L-cystine diamide, respectively. The mixtures were then allowed to incubate at 25° C. for 72 h; the solubility of L-cystine in the presence of 10 μM and 2 μM of each compound were determined using the above fluorescence assay (see FIG. 4). CDME was used as a positive control.

As shown in FIG. 1, L-cystine diamides of the present invention have better activity than CDME at increasing the aqueous solubility of L-cystine and thus inhibiting L-cystine crystallization while the corresponding methylated analogs, N,N'-dimethyl L-cystine diamides, have little effect on the aqueous solubility of L-cystine. The failure of N,N'-dimethyl L-cystine diamides to inhibit crystallization of L-cystine could be due to the fact that the N-methyl substituent adversely affected intermolecular interaction (charge-charge and hydrogen bonding) between the methylated ammonium ions (—$NH_2$(Me)) of N,N'-dimethyl L-cystine diamides and the carboxylates (—COO—) of L-cystine, so these methylated L-cystine diamides cannot bind to the specific cystine crystal surfaces and, thus, cannot inhibit crystal growth.

FIG. 1 further provides that the five L-cystine diamides, namely L-cystine dicyclopropylamide (CDCPA, LH704, IV), L-cystine bispiperidine (CDPIP, LH706, VI), L-cystine bismorpholide (CDMOR, LH707, VII), L-cystine bis(N'-methylpiperazide) (CDNMP, LH708, VIII), and L-cystine diethanolamide (CDEOA, LH709, IX), have better activity than the control compound CDME and were selected for further characterization. In order to rank the test compounds, the dose-response curves of the five L-cystine diamides was determined in comparison to CDME and calculated as $EC_{2x}$, the effective concentration required to double the solubility of L-cystine in water.

Figure 2:
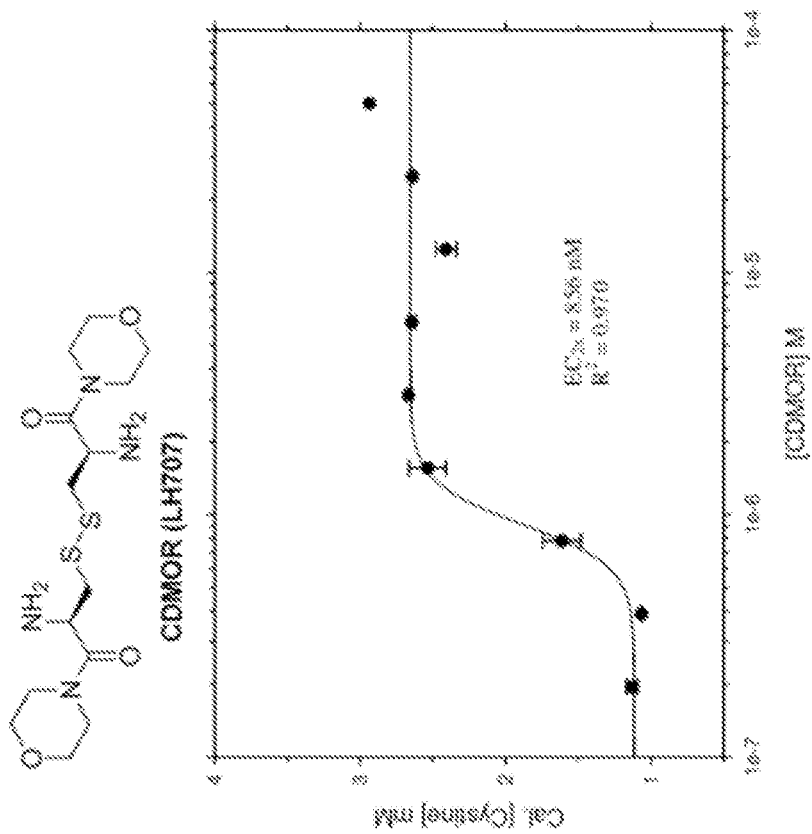
FIGS. 2 (a)-(f) provide dose-response curves of five L-cystine diamides in comparison to CDME. The figures show that the presently describe L-cystine diamides have equal or better activity than CDME at increasing the aqueous solubility of L-cystine and inhibition of L-cystine crystallization.
Figure 2:
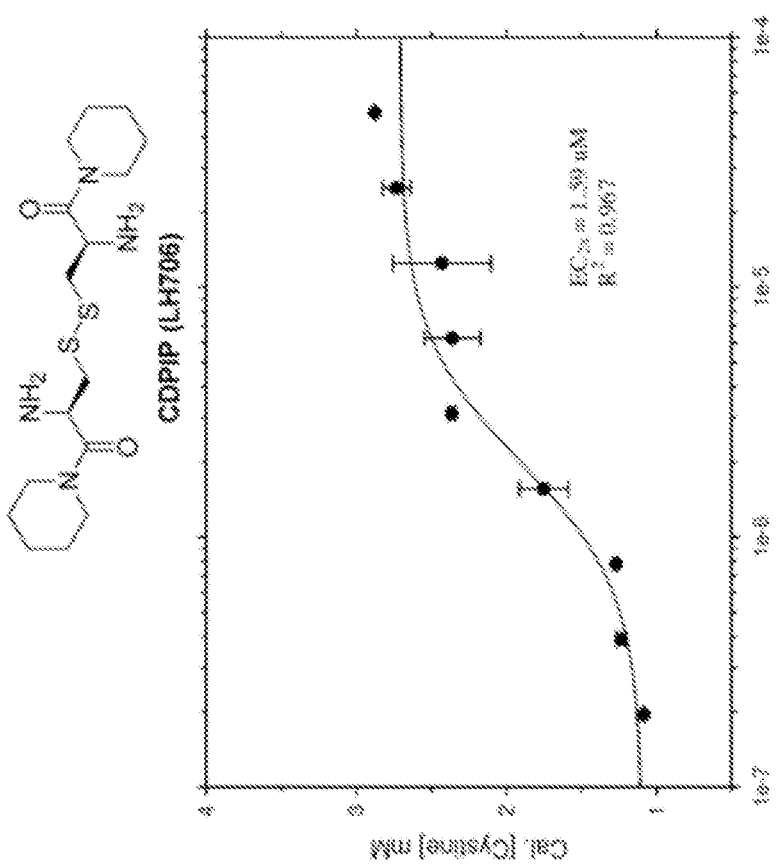
Figure 2F:
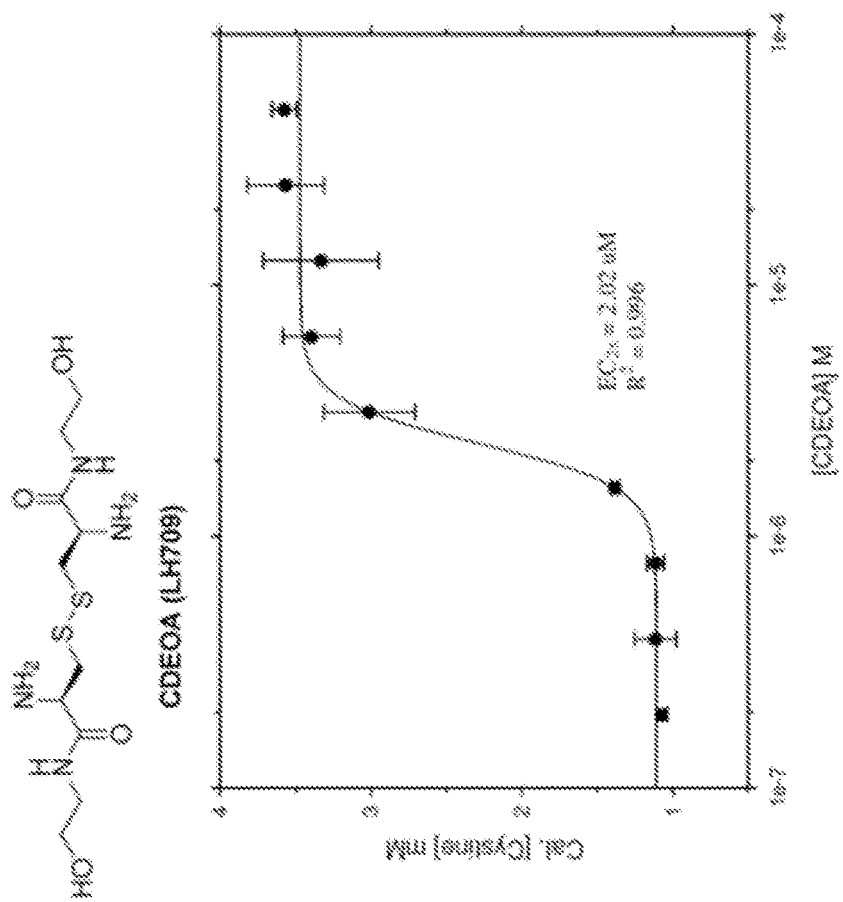
Figure 2E:
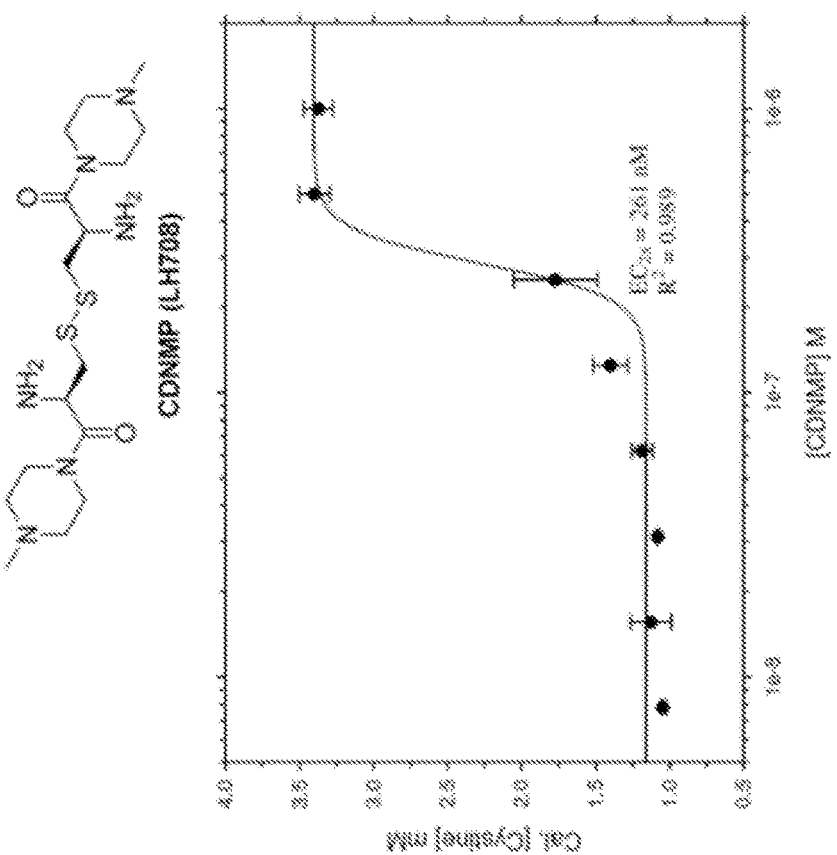

FIG. 2 and Table 1, further elaborate that all five L-cystine diamides have better $EC_{2x}$ than CDME with L-cystine bismorpholide (CDMOR, LH707, VII) and L-cystine bis(N'-methylpiperazide) (CDNMP, LH708, VIII) being the most potent. CDMOR (VII) has an $EC_2$ about 7-fold lower than CDME (0.86 vs 3.53 μM) while CDNMP (VIII) is 24-fold more potent than CDME ($EC_{2x}$ of 0.26 vs 3.53 M) at increasing the aqueous solubility of L-cystine.

TABLE 1

Effects of L-cystine diamides on the aqueous solubility of L-cystine in comparison to CDME

| LH# | Name | Structure | $EC_{2x}$ (mM)[a] | Ratio[b] |
|---|---|---|---|---|
| Control | CDME | [structure of CDME] | 6.37 | 1.0 |
| LH704 | CDCPA (IV) | [structure of CDCPA] | 3.53 | 1.8 |

TABLE 1-continued

Effects of L-cystine diamides on the aqueous solubility of L-cystine in comparison to CDME

| LH# | Name | Structure | $EC_{2x}$ (mM)[a] | Ratio[b] |
|---|---|---|---|---|
| LH706 | CDPIP (VI) | 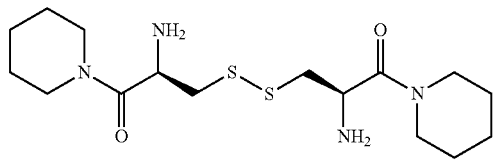 [SMILES: N[C@@H](CSSC[C@H](N)C(=O)N1CCCCC1)C(=O)N1CCCCC1] | 1.59 | 4.0 |
| LH707 | CDMOR (VII) | 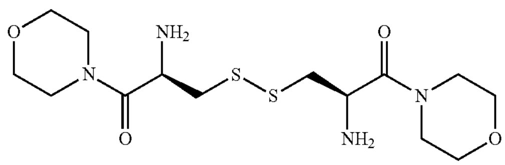 [SMILES: N[C@@H](CSSC[C@H](N)C(=O)N1CCOCC1)C(=O)N1CCOCC1] | 0.86 | 7.4 |
| LH708 | CDNMP (VIII) | 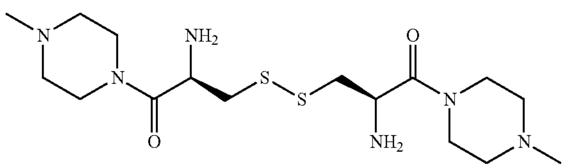 | 0.26 | 24.4 |
| LH709 | CDEOA (IX) | 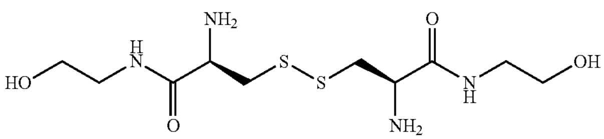 [SMILES: N[C@@H](CSSC[C@H](N)C(=O)NCCO)C(=O)NCCO] | 2.02 | 3.2 |

[a]$EC_{2x}$ refers to the concentration required to double the aqueous solubility of cystine.
[b]Ratio refers to the improvement in potency over the control CDME.

Based on these studies, the two most effective L-cystine diamide inhibitors are L-cystine bismorpholide (CDMOR, LH707, VII) and L-cystine bis (N'-methylpiperazide) (CDNMP, LH708, VIII); they are 7-24 times more effective than CDME in increasing the aqueous solubility of L-cystine and inhibiting cystine crystallization. With these two L-cystine diamides, inhibition of cystine crystallization in vitro occurs at submicromolar concentrations, which are much lower than the CDME concentration. For such reasons they are ideal candidates for treating cystinuria to prevent the formation or reduce the rate of the growth of L-cystine crystals in cystinuria patients.

Example 5—In Vivo Activity in a Genetic Mouse Model

Material and Methods
Mice

Slc3a1 knockout mice in a mixed 129/C57BL6 background were used in the studies described here. Two-month old knockout male mice for LH707 or LH708 treatment were selected. Mice at this age exhibit crystaluria but very few or no bladder stones whereas approximately 50% of three-month-old mice exhibit stones, making this the ideal window to assess the effects of treatment. Most male mice over age six months have bladder stones and some have kidney stones as well. Female knockout mice have crystaluria but no stones until age over 12 months. Mouse genotypes and gender were determined by PCR amplification of tail DNA. Based on previous observations, Slc3a1 heterozygotes have no apparent phenotype so they were used in place of wild-type mice as needed. Animal studies were conducted in accordance with Rutgers University IACUC policies.

LH707 or LH708 Administration

LH707 dihydrochloride (MW 451.43) and LH708 tetrahydrochloride (MW 550.44) were prepared fresh daily (2.9 mM in water) and 200 µl was administered to Slc3a1 knockout male mice (body weight 20 g) by gavage daily for four weeks using a 20 G disposable flexible plastic feeding needle with a soft tip (Model FTP-20-30, Instech Laboratories, Inc., Plymouth Meeting, PA).

This dose is equivalent to 29 µmol/kg (29 mg/m$^2$ assuming a body surface area of 0.007 m$^2$). To determine LH707/LH708 absorption and excretion, these compounds were administered daily for seven days and urine samples collected before and immediately after the last treatment.

Urine Collection and Analysis

Urine samples (0.15 to 1.1 ml) were collected by placing the mice in metabolic cages for four hours or longer and frozen at −20° C. The four-week treatment samples were analyzed for amino acids by ion exchange chromatography on a Biochrom analyzer (Biochrom US, Holliston, MA) and the amino acid levels normalized to umol/mg creatinine. The seven-day treatment samples were analyzed for LH707 and LH708 by LC-MS (see below).

Micro-Computed Tomography

Mice were sacrificed after urine collection and the bladder and kidneys removed and placed in 10% formalin. The bladder was scanned ex vivo using a SkyScan 1172 micro CT scanner with a 50 mm field of view (Bruker Corp., Billerica, MA). Images were taken with an 11 Mp Hamamatsu camera with a pixel size of 11.51 pam. The source voltage and current ranged between 40-45 kV and 220-250 µA, respectively, and the scan time was approximately 30 min. The SkyScan reconstruction program NRecon was used for image reconstruction. The output images were imported into the Bruker CT-Analyzer (CTAn) program (version 1.13). This application was evaluated for the assessment of quantitative parameters such as bladder volume, stone volume, and stone number from the scanned 3D datasets.

Estimation of Stone Size and Number

Figure 5:
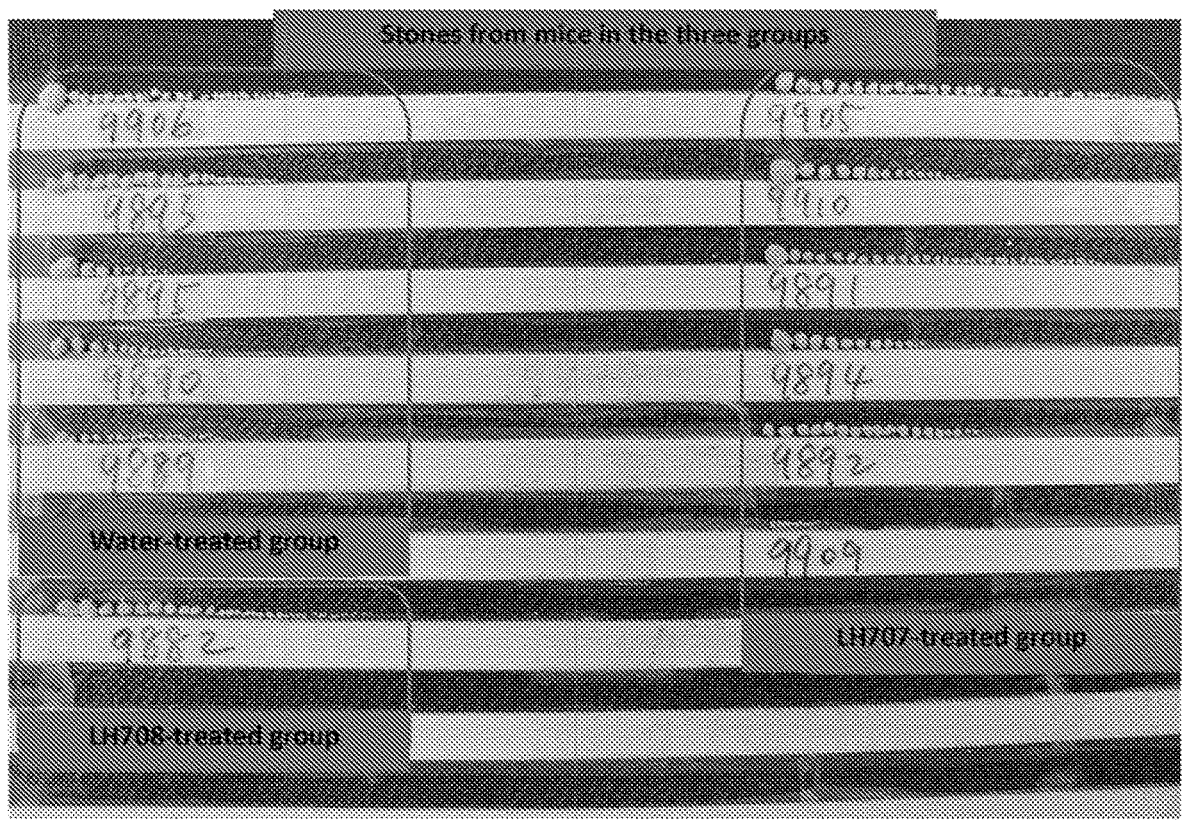
FIG. 5 provides pictures of stones found in mice treated.

After micro CT scanning, bladders were weighed and the stones removed, weighed, counted, and measured in the longest dimension (see FIG. 5).

Analysis of Urine Samples by UPLC-MS

It was determined that the concentrations of LH7071LH708 in the urine samples collected using LC-MS/MS in positive MRM mode (LH707, 379.0→188.9; LH708, 203.1→4101.3) on a Transcend LX2 system (Thermo Fisher, Waltham, MA) coupled to an API 4000 (AB Sciex, Framingham, MA). Chromatographic separation was achieved with a HILIC column (2.1×50 mm, 5 µm, Waters Corporation, Huntingdon Valley, PA) using a water (A)/ACN (B) mobile phase system containing 0.1% formic acid (v/v). The gradient was performed at a flow rate of 750 µL/min as follows: 95% B for 90 s, 95 to 5% B in 42 s, 5% B for 30 s.

Data Analysis and Discussion

Fisher's exact test was used to assess the number of mice with and without stones in each of the two groups. A two-tailed t-test was used with unequal variance to assess differences in bladder weight, stone weight, and stone number between the LH707/LH708- and water-treated groups. Significance level was set at 5%.

Based on the results, inventors concluded that LH708 has a better efficacy at inhibiting cystine stone formation, as only 1 out 7 LH708-treated mice showed stones in their bladder. Further, the concentration of cysteine in mouse urine was significantly increased as compared to before treatment. Finally, there were no significant changes in the urine concentration of other amino acids such as ornithine, lysine, arginine, proline, valine, leucine and phenylalanine.

Figure 6:
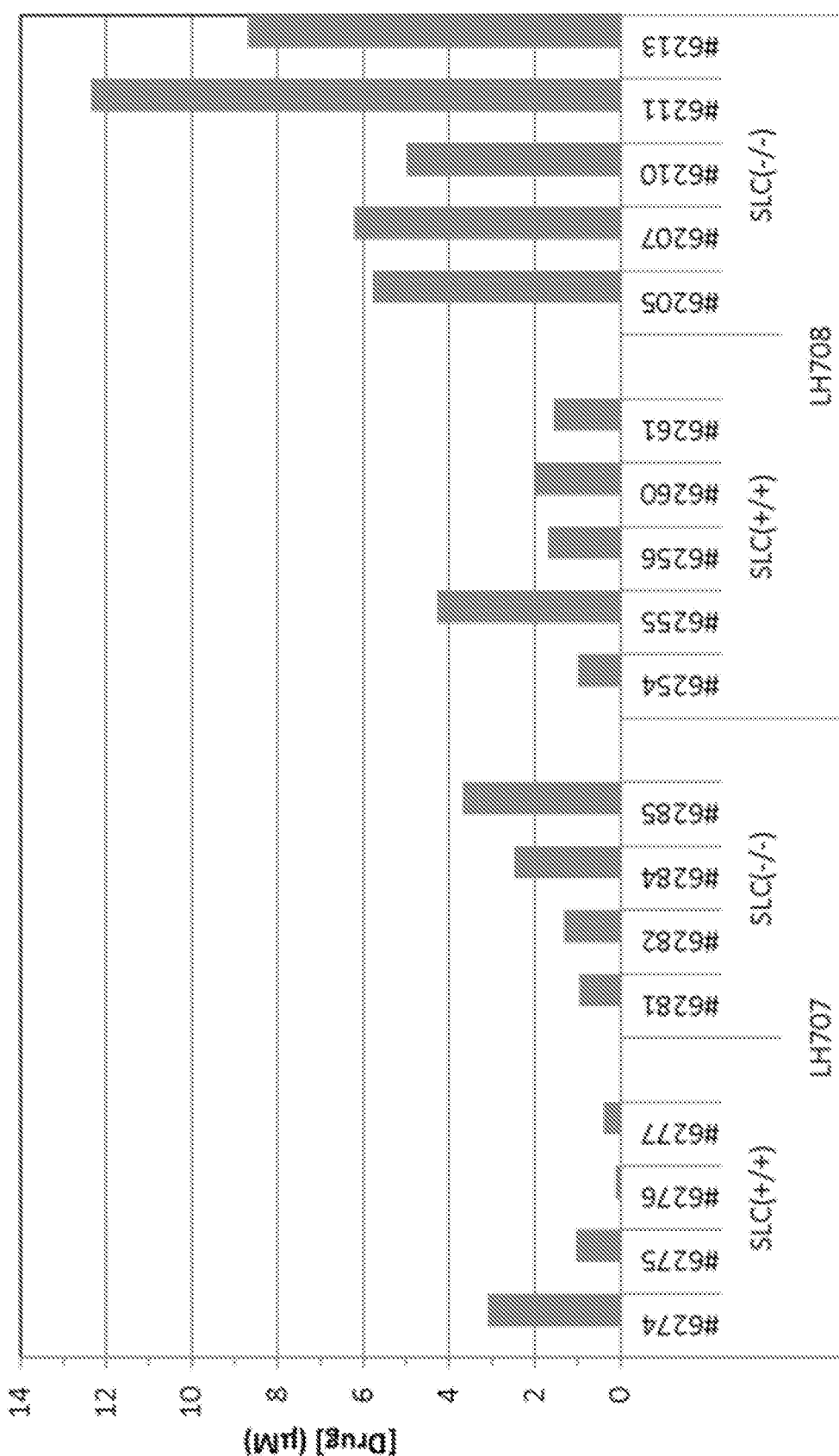
FIG. 6 provides the drug concentration in mouse urine after 7 daily oral dosing of LH707 and LH708.

Initially, inventors observed that there was no trace of the test compounds in urine samples collected prior to oral dosing. However, after the completion of the dosing regimen significant amount of the test compounds were found in the urine of the participating mice (see FIG. 6). Existence of micromolar concentrations of LH707 and LH708 in each mouse after such dosing suggests that the compounds are readily bioavailable when administered orally.

Figure 7:
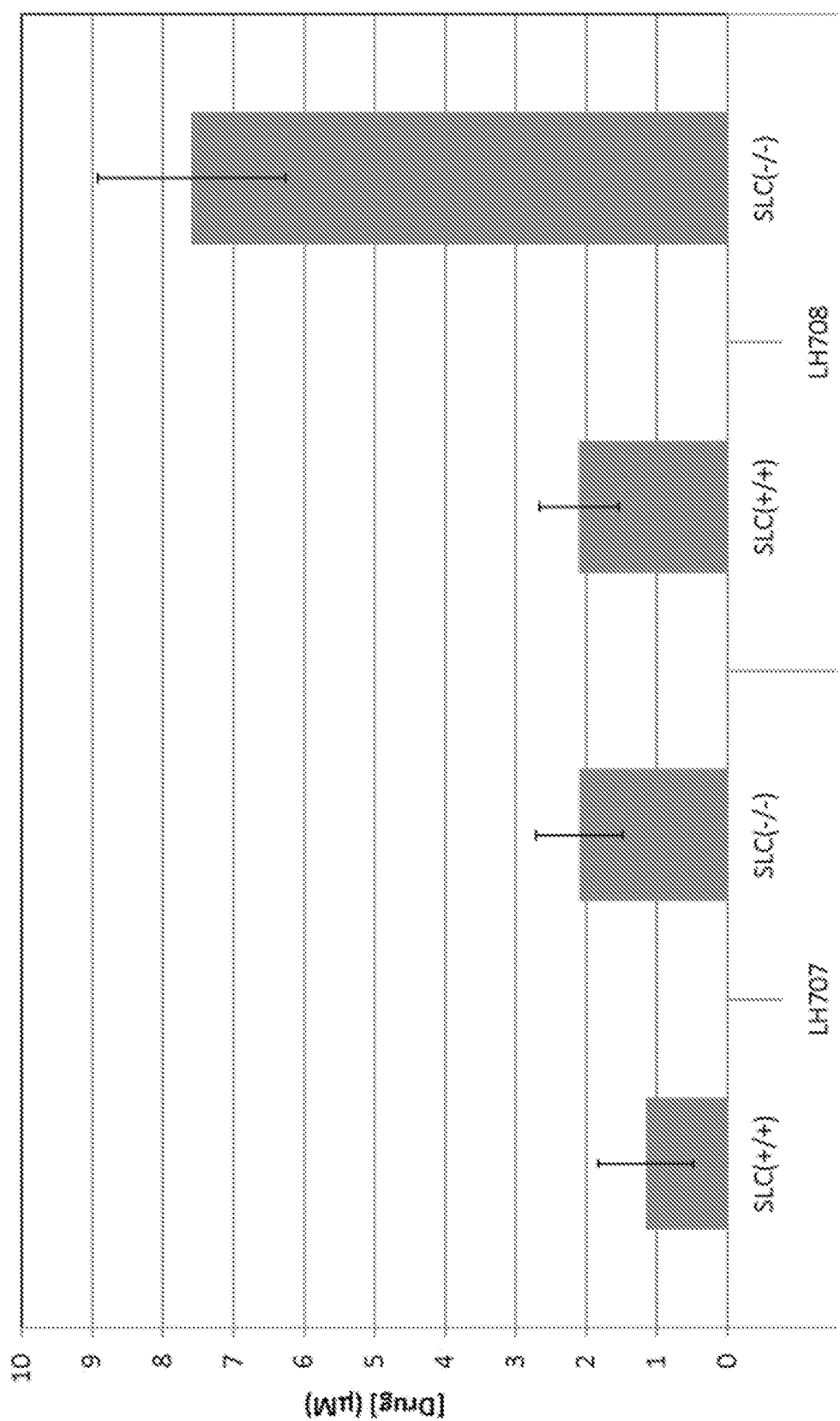
FIG. 7 provides the graph of the average compound concentration in mouse urine after 7 daily oral dosing of LH707 and LH708 in Slc3a1 knockout mice and the control mice (the average and standard error were derived from the 5 or 4 mice treated with LH707 and LH708, respectively).

Surprisingly, significantly higher concentrations of LH708 were found in cysteineuria mice; the Slc3a1 knockout mice, than in control or normal mice (see FIG. 7). As LH708 has a polyamine core structure, it is concluded that LH708 may be absorbed similar to polyamines such as spermine or spermidine, rather than to cystine. This is an unexpected observation, as it suggests that other transporters (like polyamine transporters) are likely elevated in cystineuric mice (i.e. after knocking out the SLC3A1 gene) which worked in favor of LH708 availability, but not in LH707.

Finally, the higher volumes of urine collected in LH708-treated mice as compared to before treatment, as shown in FIG. 8 suggests that LH708 could also be having diuretic effects as an additional benefit. As there were no significant changes in the urine concentration of other amino acids such as ornithine, lysine, arginine, proline, valine, leucine and phenylalanine, those of ordinary skill in the art can extrapolate that the diuretic effects are attributed to the compounds administered and/or the rise of urine cystine concentration during the treatment course (see FIG. 9).

While certain of the embodiment of the present invention have been described and specifically exemplified above, it is not intended that the invention be limited to such embodiments. Various modifications may be made thereto without departing from the scope and spirit of the present invention as set forth in the following claims. All such modifications coming within the scope of the present claims are intended to be included herein.

We claim:

1. A compound of formula (A):

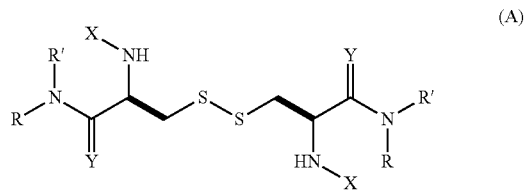

and pharmaceutically acceptable salts, solvates and prodrugs thereof wherein
a set of X and each R and R' pair is selected from (i) or (ii) or (iii);
(i) X is alkyl, R and R' are independently selected from the group consisting of hydrogen, substituted or unsubstituted alkyl, substituted or unsubstituted alkenyl, substituted or unsubstituted alcohol, substituted or unsubstituted aryl, substituted or unsubstituted cycloalkyl, substituted or unsubstituted heterocyclic, and substituted or unsubstituted heteroaryl, or
(ii) X is hydrogen, R and R' are independently selected from the group consisting of hydrogen, substituted or unsubstituted alkenyl, substituted or unsubstituted alcohol, substituted or unsubstituted cycloalkyl, substituted or unsubstituted heterocyclic, and substituted or unsubstituted heteroaryl, or
(iii) X is hydrogen or alkyl, R and R' together form a substituted or unsubstituted heterocyclic ring structure, or a substituted or unsubstituted heteroaryl ring structure,
provided that
(a) when R and R' together form the substituted heterocyclic ring structure, the substituent is not cyano; and
(b) R and R' of at least one pair together form a heterocyclic ring structure, wherein the ring structure has a formula (B),

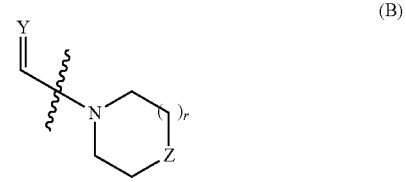

wherein Z is CR"-Q, N-Q or O;
Q and R" are independently selected from the group consisting of hydrogen, substituted or unsubstituted alkyl, substituted or unsubstituted alkenyl, substituted or unsubstituted aryl, substituted or unsubstituted heteroaryl, substituted or unsubstituted cycloalkyl, and substituted or unsubstituted cycloalkenyl; and r is 0-4;

and Y is O or S,
provided that the compound is not

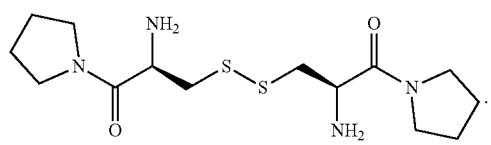 [SMILES: N[C@@H](CSSC[C@H](N)C(=O)N1CCCC1)C(=O)N1CCCC1]

2. The compound of claim 1, wherein Z is N-Q; r is 1-3; and Q is hydrogen or an alkyl.

3. The compound of claim 1, wherein said structure (B) is selected from the group consisting of:

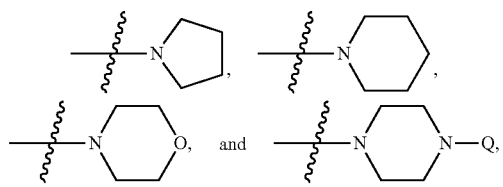

and Q is hydrogen or a lower alkyl.

4. A pharmaceutical composition comprising a pharmaceutically effective amount of the compound of claim 1 or a pharmaceutically acceptable salt thereof.

5. A compound selected from the group consisting of

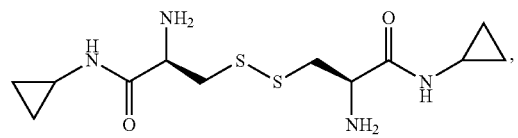
(IV)

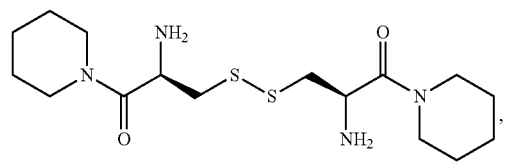
(VI)

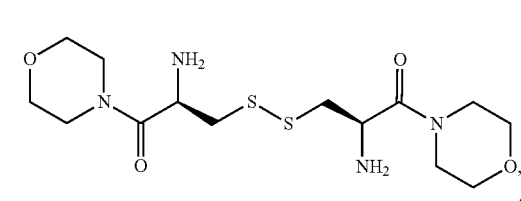
(VII)

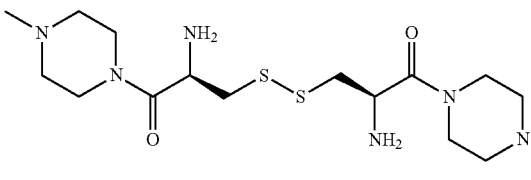
(VIII)

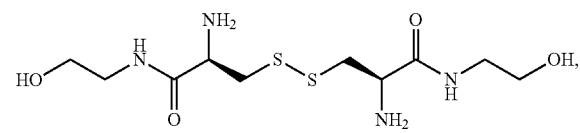
(IX)

-continued

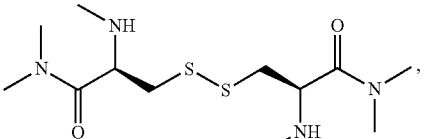
(X)

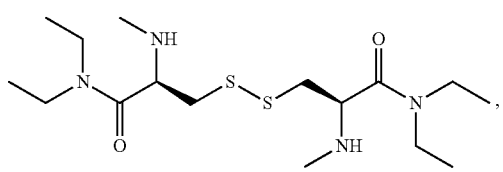
(XI)

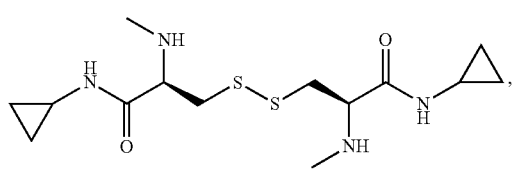
(XII)

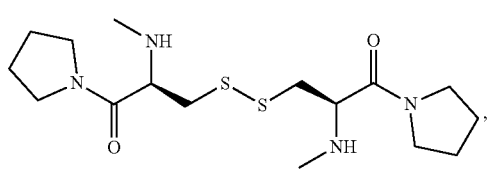
(XIII)

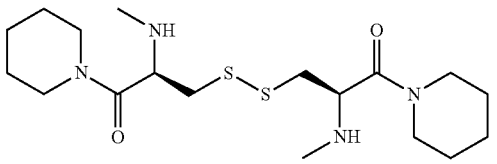
(XIV)

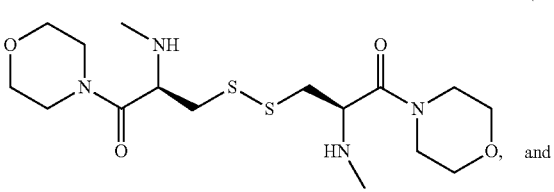
(XV)

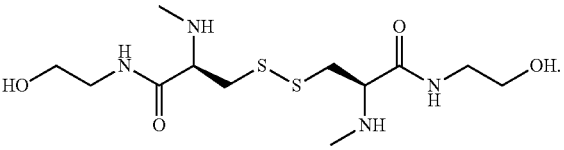
(XVI)

6. The compound of claim 5, which is

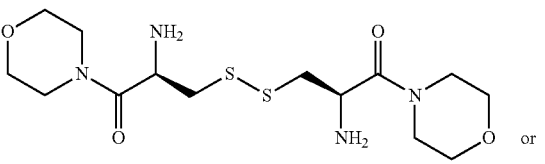
(VII)

or

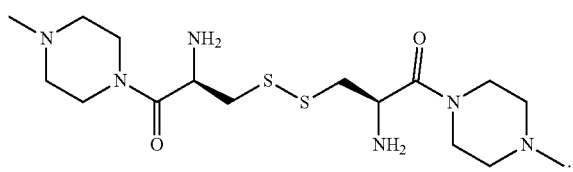
(VIII)
7. The pharmaceutical composition of claim 4, wherein the compound is
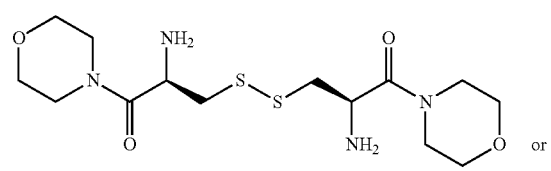
(VII)
or
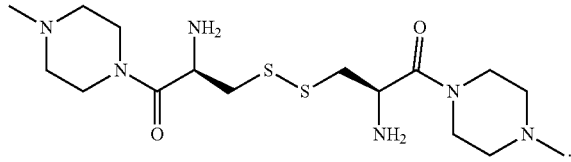
(VIII)
8. The compound of claim 6, which is
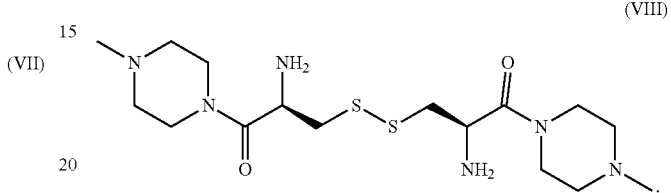
(VIII)
* * * * *